United States Patent
Farha et al.

(10) Patent No.: US 9,562,118 B2
(45) Date of Patent: Feb. 7, 2017

(54) TRANSITION METAL COMPLEXES SUPPORTED ON METAL-ORGANIC FRAMEWORKS FOR HETEROGENEOUS CATALYSTS

(71) Applicant: Northwestern University, Evanston, IL (US)

(72) Inventors: Omar K. Farha, Glenview, IL (US); Joseph T. Hupp, Northfield, IL (US); Massimiliano Delferro, Chicago, IL (US); Rachel C. Klet, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/824,955

(22) Filed: Aug. 12, 2015

(65) Prior Publication Data
US 2016/0046738 A1    Feb. 18, 2016

Related U.S. Application Data

(60) Provisional application No. 62/036,510, filed on Aug. 12, 2014.

(51) Int. Cl.
*C07F 7/00* (2006.01)
*C08F 10/14* (2006.01)

(52) U.S. Cl.
CPC .............. *C08F 10/14* (2013.01); *C07F 7/00* (2013.01); *C07F 7/006* (2013.01)

(58) Field of Classification Search
CPC .............. C07F 7/00; C07F 7/006; C08F 10/14
USPC .......................................... 556/28; 585/523
See application file for complete search history.

(56) References Cited

U.S. PATENT DOCUMENTS

| | | | |
|---|---|---|---|
| 8,133,301 | B2 | 3/2012 | Hwang et al. |
| 8,518,264 | B2 | 8/2013 | Kiener et al. |
| 8,536,358 | B2 | 9/2013 | Kim et al. |

OTHER PUBLICATIONS

International Search Report for PCT/US2015/044893 (WO 2016/025624) published Feb. 18, 2016.*
Written Opinion of the International Searching Report for PCT/US2015/044893 (WO 2016/025624) published Feb. 18, 2016.*
Mondloch, J. et al., "Vapor-Phase Metalation by Atomic Layer Deposition in a Metal-Organic Framework", Journal of the American Chemical Society, 2013, vol. 135, 10294-10297.
Bon, Volodymyr et al., "Zr- and Hf-Based Metal-Organic Frameworks: Tracking Down the Polymorphism", Crystal Growth and Design, 2013, 13, 1231-1237.
Coperet, C. et al., "Homogeneous and Heterogeneous Catalysis: Bridging the Gap through Surface Organometallic Chemistry", Angew. Chem. Int. Ed. 2003, 42, 156.
Stalzer, M. et al., "Supported Single-Site Organometallic Catalysts for the Synthesis of High-Performance Polyolefins", Catal. Lett. 2015, 145, 3.
Furukawa, H. et al., "The Chemistry and Applications of Metal-Organic Frameworks", Science 2013, 341, 1230444.

(Continued)

*Primary Examiner* — Porfirio Nazario Gonzalez
(74) *Attorney, Agent, or Firm* — Reinhart Boerner Van Deuren s.c.

(57) ABSTRACT

A robust mesoporous metal-organic framework comprising a hafnium-based metal-organic framework and a single-site zirconium-benzyl species is provided. The hafnium, zirconium-benzyl metal-organic framework is useful as a catalyst for the polymerization of an alkene.

18 Claims, 25 Drawing Sheets

(56) References Cited

OTHER PUBLICATIONS

Cavka, J. H. et al., A New Zirconium Inorganic Building Brick Forming Metal Organic Frameworks with Exceptional Stability, J. Am. Chem. Soc. 2008, 130, 13850.
Feng, D. et al., "Zirconium-Metalloporphyrin PCN-222: Mesoporous Metal-Organic Frameworks with Ultrahigh Stability as Biomimetic Catalysts", Angew. Chem. Int. Ed. 2012, 51, 10307.
Morris, W. et al., "Synthesis, Structure, and Metalation of Two New Highly Porous Zirconium Metal-Organic Frameworks", Inorg. Chem. 2012, 51, 6443.
Furukawa, H. et al., "Water Adsorption in Porous Metal-Organic Frameworks and Related Materials", J. Am. Chem. Soc. 2014, 136, 4369.
Marenich, A. et al., "Charge Model 5: An Extension of Hirshfeld Population Analysis for the Accurate Description of Molecular Interactions in Gaseous and Condensed Phases", J. Chem. Theor. Comput. 2012, 8, 527-541.
Planas, N. et al., "Defining the Proton Topology of the Zr6-Based Metal-Organic Framework NU-1000", J. Phys. Chem. Lett. 2014, 5, 3716.
Yang, D. et al., "Metal-Organic Framework Nodes as Nearly Ideal Supports for Molecular Catalysts: NU-1000- and UiO-66-Supported Iridium Complexes", J. Am. Chem. Soc. 2015.
Deria, P. et al., "Perfluoroalkane Functionalization of NU-1000 via Solvent-Assisted Ligand Incorporation: Synthesis and CO2 Adsorption Studies", J. Am. Chem. Soc. 2013, 135, 16801.
Deria, P. et al., "Versatile functionalization of the NU-1000 platform by solvent-assisted ligand incorporation", Chem. Commun. 2014, 50, 1965.
Meilikhov, M. et al., "Reduction of a Metal-Organic Framework by an Organometallic Complex: Magnetic Properties and Structure of the Inclusion Compound [(n5-C5H5)2Co]0.5@MIL-47(V)", Angew. Chem. Int. Ed. 2010, 49, 6212.
Kalidindi, S. et al., "Metallocenes@COF-102: organometallic host-guest chemistry of porous crystalline organic frameworks" Chem. Commun. 2011, 47, 8506.
Zhang, Z. et al., "Template-Directed Synthesis of Nets Based upon Octahemioctahedral Cages That Encapsulate Catalytically Active Metalloporphyrins", J. Am. Chem. Soc. 2011, 134, 928.
Li, B. et al., "Metal-Cation-Directed de Novo Assembly of a Functionalized Guest Molecule in the Nanospace of a Metal-Organic Framework", J. Am. Chem. Soc. 2014, 136, 1202.
Yoon, M. et al., "Homochiral MetalOrganic Frameworks for Asymmetric Heterogeneous Catalysis", Chem. Rev. 2011, 112, 1196.
Meilikhov, M. et al., "Turning MIL-53(Al) Redox-Active by Functionalization of the Bridging OH-Group with 1,1'-Ferrocenediyl-Dimethylsilane", J. Am. Chem. Soc. 2009, 131, 9644.
Larabi, C. et al. at the "Titration of Zr3(u-OH) Hydroxy Groups at the Cornerstones of Bulk MOF UiO-67, [Zr6O4(OH)4(biphenyldicarboxylate)6], and Their Reaction with [AuMe(PMe3)]", Eur. J. Inorg. Chem. 2012, 2012, 3014.
Nguyen, H. et al., "Vanadium-Node-Functionalized UiO-66: A Thermally Stable MOF-Supported Catalyst for the Gas-Phase Oxidative Dehydrogenation of Cyclohexene", ACS Catalysis 2014, 4, 2496.
Bassett, J.M. et al., "Metathesis of Alkanes and Related Reactions", Acc. Chem. Res. 2010, 43, 323.
Ballard, D., "Pi and Sigma Transition Metal Carbon Compounds as Catalysts for the Polymerization of Vinyl Monomers and Olefins" Adv. Catal. 1973, 23, 263.

Yermakov, Y. et al., "One-Component Catalysts for Polymerization of Olefins", Adv. Catal. 1975, 24, 173.
Williams, L. et al., "Surface structural-chemical characterization of a single-site d0 heterogeneous arene hydrogenation catalyst having 100% active sites", Proc. Natl. Acad. Sci. U.S.A. 2013, 110, 413.
Gu, W. et al., "Benzene Selectivity in Competitive Arene Hydrogenation: Effects of Single-Site Catalyst—Acidic Oxide Surface Binding Geometry", J. Am. Chem. Soc. 2015, 137, 6770.
Stylianou, K. et al., "A Guest-Responsive Fluorescent 3D Microporous Metal-Organic Framework Derived from a Long-Lifetime Pyrene Core", J. Am. Chem. Soc. 2010, 132, 4119.
Popoff, N. et al., "Small Changes Have Consequences: Lessons from Tetrabenzyltitanium and -zirconium Surface Organometallic Chemistry", Chem. Eur. J. 2013, 19, 964.
Popoff, N. et al., "Well-Defined Silica-Supported Zirconium-Benzyl Cationic Species: Improved Heterogenization of Single-Site Polymerization Catalysts", Eur. J. Inorg. Chem. 2014, 2014, 888.
Rong, Y. et al., "Highly Variable Zr—CH2—Ph Bond Angles in Tetrabenzylzirconium: Analysis of Benzyl Ligand Coordination Modes", Organometallics 2012, 31, 8208.
Chen, E. et al., "Cocatalysts for Metal-Catalyzed Olefin Polymerization: Activators, Activation Processes, and Structure-Activity Relationships", Chem. Rev. 2000, 100, 1391.
Zucchini, U. et al., "Synthesis and Properties of Some Titanium and Zirconium Benzyl Derivatives", Organomet. Chem. 1971, 26, 357-372.
Ressler, T. et al., "WinXAS: a Program for X-ray Absorption Spectroscopy Data Analysis under MS-Windows", Radiat. 1998, 5, 118-122.
Perdew, J. et al., "Accurate and simple analytic representation of the electron-gas correlation energy", Phys. Rev. B 1992, 45, 13244-13249.
Perdew, J. et al., "Generalized Gradient Approximation Made Simple", Phys. Rev. Lett. 1996, 77, 3865-3868.
Perdew, J. et al., "Rationale for mixing exact exchange with density functional approximations", J. Chem. Phys. 1996, 105, 9982-9985.
Kresse, G. et al., "Efficient iterative schemes for ab initio total-energy calculations using a plane-wave basis set", Phys. Rev. B 1996, 54, 11169-11186.
Kresse, G. et al., "Ab initio molecular-dynamics simulation of the liquid-metal-amorphous-semiconductor transition in germanium", Phys. Rev. B 1994, 49, 14251-14269.
Kresse, G. et al., "Ab. initio molecular dynamics for liquid metals", Phys. Rev. B 1993, 47, 558-561.
Kresse, G. et al., "Efficiency of ab-initio total energy calculations for metals and semiconductors using a plane-wave basis set", Comput. Mater. Sci. 1996, 6, 15-50.
Zhao, Y. et al., "A new local density functional for main-group thermochemistry transition metal bonding, thermochemical kinetics, and noncovalent interactions", J. Chem. Phys. 2006, 125, 194101.
Weigend, F. et al., "Balanced basis sets of split valence, triple zeta valence and quadruple zeta valence quality for H to Rn: Design and assessment of accuracy", Phys. Chem. Chem. Phys., 2005, 7, 3297.
Pangborn, A. et al., "Safe and Convenient Procedure for Solvent Purification", Organometallics, 1996, 15, 1518-1520.
Lee, J. et al., "Metal-organic framework materials as catalysts", Chemical Society Reviews, 2009, 38, 1450-1459.
Beyzavi M. et al., "A Hafnium-Based Metal-Organic Framework as an Efficient and Multifunctional Catalyst for Facile CO2 Fixation and Regioselective and Enantioretentive Epoxide Activation", J. Am. Chem. Soc., 2014, 136, 15861-15864.

* cited by examiner

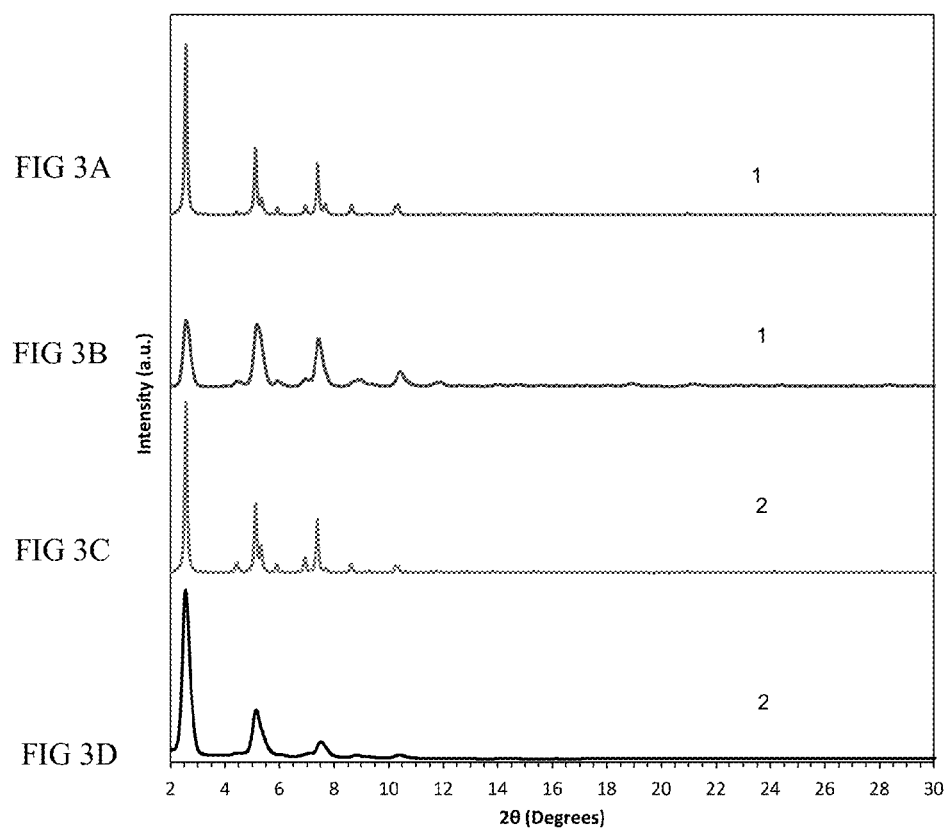

FIG 4A
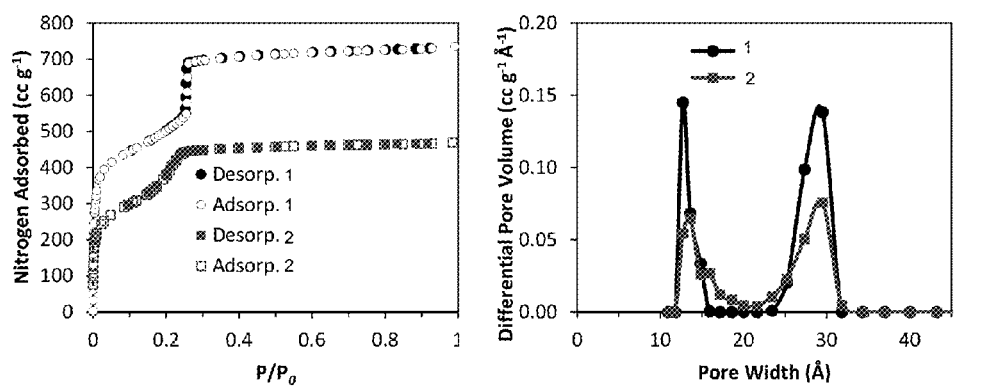
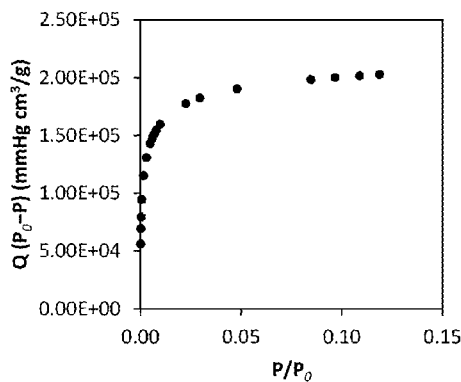
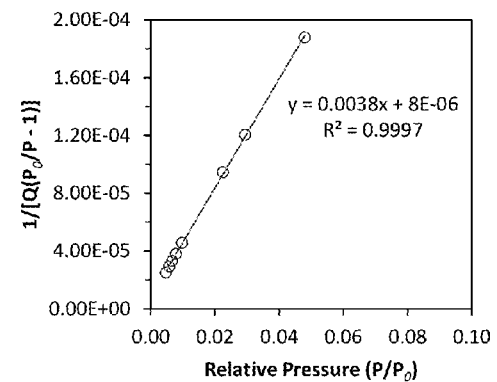
FIG 4B  FIG 4C

FIG 9A
FIG 9B
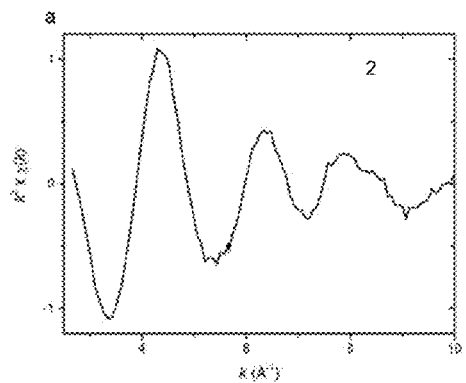
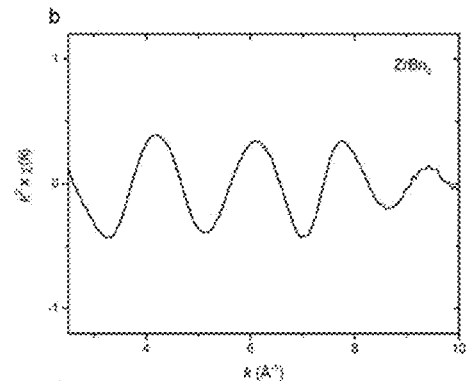
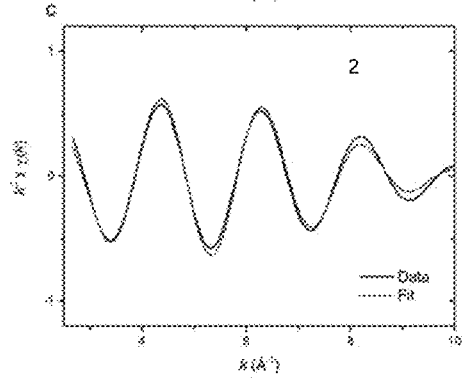
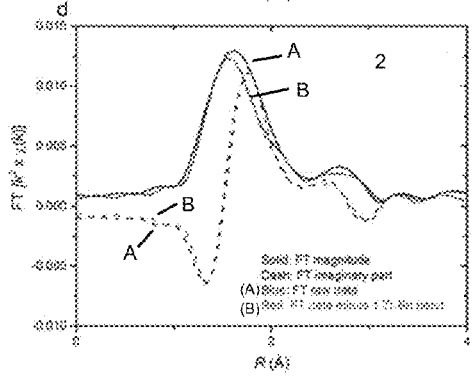
FIG 9C
FIG 9D

TRANSITION METAL COMPLEXES SUPPORTED ON METAL-ORGANIC FRAMEWORKS FOR HETEROGENEOUS CATALYSTS

This application claims priority benefit from application Ser. No. 62/036,510 filed Aug. 12, 2014—the entirety of which is incorporated herein by reference.

This invention was made with government support under DE-SC0012702 awarded by the U.S. Department of Energy. The government has certain rights in the invention.

FIELD OF THE INVENTION

The present invention relates generally to a robust mesoporous metal-organic framework. In particular, the present invention relates to a hafnium-based metal-organic framework used as a well-defined platform for supporting a single-site zirconium-benzyl species. The hafnium, zirconium-benzyl metal-organic framework is useful as a catalyst.

BACKGROUND OF THE INVENTION

Heterogeneous catalysts have many advantages over their homogeneous counterparts including recyclability, easier separation from product streams and, often, greater stability. Accordingly, nearly 80% of industrial processes employ heterogeneous catalysts (*Synthesis of Solid Catalysts;* de Jong, K. P., Ed.; Wiley-VCH: Germany, 2009). Despite their broad implementation, the design and synthesis of new highly active and selective heterogeneous catalysts remains an important goal. Typically, heterogeneous catalysts are supported on complex materials in which it is difficult to characterize active sites and establish structure-activity relationships in order to rationally design improved catalytic species (Boudart, M.; Djéga-Mariadassou, G. *Kinetics of Heterogeneous Catalytic Reactions;* Princeton University Press: Princeton, N.J., 1984; Thomas, J. M.; Thomas, W. J. *Principles and Practice of Heterogeneous Catalysis;* VCH: New York, 1997). Thus, there is still a need for methods to synthesize heterogeneous catalysts in a controlled and well-defined manner and for their computational characterization.

One approach to access well-defined "single-site" heterogeneous catalysts is to employ atomically defined and periodic supports (Coperet, C. et al., *Angew. Chem. Int. Ed.* 2003, 42, 156; Stalzer, M. M. et al., *Catal. Lett.* 2015, 145, 3). It is desired to utilize a chemically and thermally robust metal-organic framework (MOF) in lieu of a traditional metal oxide or activated carbon as a platform for supporting homogeneous complexes. MOFs are three-dimensional, crystalline, porous materials composed of inorganic nodes (metal ions or clusters) and organic linkers, and have been investigated for many applications (Furukawa, H. et al., *Science* 2013, 341, 1230444). Given the periodic structure of MOFs and the potential to determine the precise position of atoms using single X-ray diffraction studies, they are considered to be promising and underutilized catalytic supports.

One class of MOFs that has gained recognition for their exceptional stability is Zr- and Hf-based MOFs, which consist of $Zr_6$ or $Hf_6$ nodes $[M_6(\mu_3-O)_4(\mu_3-OH)_4(OH)_4(H_2O)_4$, M=Zr, Hf] and the tetra-carboxylate linker 1,3,6,8-tetrakis(p-benzoate)pyrene ($H_4TBAPy$) (Cavka, J. H. et al., *Angew. Chem. Int. Ed.* 2012, 51, 10307; Morris, W. et al., *Inorg. Chem.* 2012, 51, 6443; Furukawa, H. et al., *J. Am. Chem.* Soc. 2014, 136, 4369; Mondloch, J. E. et al., *J. Am. Chem. Soc.* 2013, 135, 10294; Beyzavi, M. H. et al., *J. Am. Chem. Soc.* 2014, 136, 15861). These MOFs exhibit large 29-30 Å hexagonal mesopores to facilitate mass transport (of both catalyst precursors and reactants/products) throughout the material, and accessible grafting sites in the form of —OH and —$OH_2$ groups, the topology of which has been experimentally and computationally determined (Planas, N. et al., *J. Phys. Chem. Lett.* 2014, 5, 3716). It has been shown that these anchoring sites can be functionalized via atomic layer deposition (ALD), wet impregnation with organometallic precursors, and with carboxylate groups via ligand attachment (Yang, D. et al., *J. Am. Chem. Soc.* 2015; Deria, P. et al., *J. Am. Chem. Soc.* 2013, 135, 16801; Deria, P. et al., *Chem. Commun.* 2014, 50, 1965.

Incorporation of metal complexes into MOFs has been explored using three methodologies: (1) inclusion of metal complexes into MOF pores; (2) covalent attachment onto organic linkers; and (3) covalent attachment to functional groups associated with the inorganic nodes (Meilikhov, M. et al., *Angew. Chem. Int. Ed.* 2010, 49, 6212; Kalidindi, S. B. et al., *Chem. Commun.* 2011, 47, 8506; Zhang, Z. et al., *J. Am. Chem. Soc.* 2011, 134, 928; Li, B. et al., *J. Am. Chem. Soc.* 2014, 136, 1202; Lee, J. et al., *Chem. Soc. Rev.* 2009, 38, 1450; Yoon, M. et al., *Chem. Rev.* 2011, 112, 1196; Meilikhov, M. et al., *J. Am. Chem. Soc.* 2009, 131, 9644; Larabi, C. et al., *Eur. J. Inorg. Chem.* 2012, 2012, 3014; Nguyen, H. G. T. et al., *ACS Catalysis* 2014, 4, 2496. Compared to inclusion complexes, covalent attachment is more likely to lead to catalytic materials broadly useful for demanding heterogeneous reactions. It is believed that attachment to the node is more likely to lead to well-defined and periodic heterogeneous species given that installing appropriate grafting sites on linkers in a regular and controlled manner is often difficult.

Full characterization and preliminary olefin polymerization activity of an organozirconium precursor covalently attached to a Hf-based MOF (Scheme 1) has previously been reported (Bassett, J. M. et al., *Acc. Chem. Res.* 2010, 43, 323). Supported group 4 metal-alkyl species have been extensively investigated for nearly four decades due to their importance in olefin polymerization, hydrogenation, and other catalytic reactions (Ballard, D. G. H. *Adv. Catal.* 1973, 23, 263.; Yermakov, Y. et al., *Adv. Catal.* 1975, 24, 173; Williams, L. A. et al., *Proc. Natl. Acad. Sci. U.S.A.* 2013, 110, 413; Gu, W. et al., *J. Am. Chem. Soc.* 2015, 137, 6770).

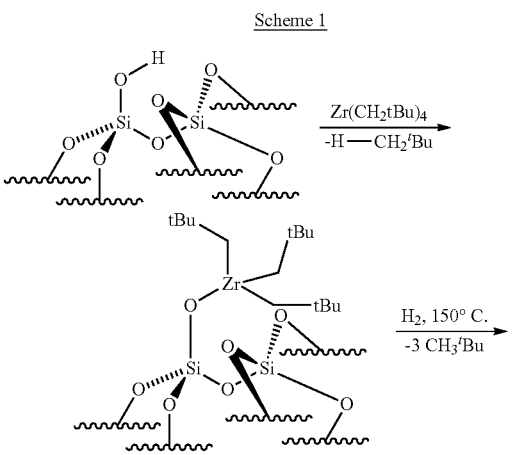

Scheme 1

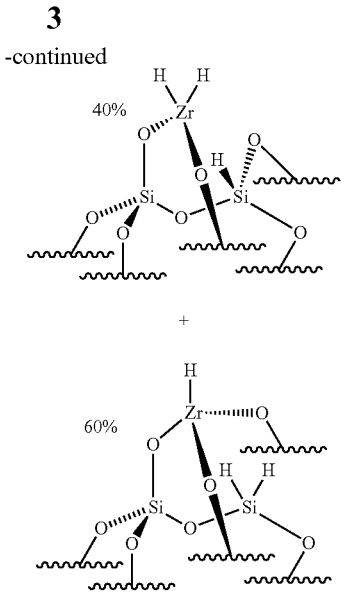

It is therefore desirable to provide for the synthesis, full characterization, and preliminary olefin polymerization activity of an organozirconium precursor covalently attached to a group 4 metal-based, e.g. hafnium, metal-organic framework.

SUMMARY OF THE INVENTION

In light of the foregoing, it is an object of the present invention to provide a compound comprising a reaction product of a metal-organic framework and a transition metal complex, such as, but not limited to, zirconium tetrabenzyl. For example, without limitation, the metal of such a framework is a group 4 metal such as hafnium (Hf).

It is further an object of the invention to provide a method of using a metal-organic framework for alkene polymerization, the method comprising providing a compound comprising a reaction product of a transition metal-based metal-organic framework and a single-site zirconium-benzyl derivative; and contacting the compound with an alkene under at least one of a pressure and temperature sufficient to polymerize the alkene.

Accordingly, it will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

Other objects, features, benefits and advantages of the present invention will be apparent from this summary and the following descriptions of certain embodiments, and will be readily apparent to those skilled in the art. Such objects, features, benefits and advantages will be apparent from the above as taken into conjunction with the accompanying examples, data, and all reasonable inferences to be drawn therefrom. The disclosures in this application of all articles and references, including patents, are incorporated herein by reference.

BRIEF DESCRIPTION OF THE DRAWINGS

FIGS. 3A-D provide PXRD patterns of 1 and 2. A) is a simulated PXRD patterns of 1; B) is an experimental patterns of 1; C) is a simulated pattern of 2; and D) is an experimental pattern of 2.

FIGS. 4A-C are A) $N_2$ adsorption isotherms and DFT pore size distributions (using a carbon slit pore model with a $N_2$ DFT kernel) for 1 (dark) and 2 (light); B) Rouquerol plot; and C) BET plot for 2 ($N_2$ isotherm black circles). The $R^2$ value from the BET plot is 0.99967 and the y-intercept is $8.0 \times 10^{-6}$.

FIGS. 9A-D show Zr K-edge $k^2$ weighted EXAFS of (A) 2; (B) $ZrBn_4$; (C) the isolated first shell fit of 2 with a Zr—O coordination number of 4 ($k^2$: Δk=2.7–10.9 $Å^{-1}$; ΔR=1.1–1.9 Å); and (D) the Fourier transform (FT) of the k-space spectrum of 2 and the FT of the k-space spectrum of 2 after subtraction of 0.25 times chi($ZrBn_4$), wherein ($k^2$: Δk=2.7–10.9$Å^{-1}$).

DETAILED DESCRIPTION OF THE INVENTION

Accordingly, a non-limiting embodiment of the invention is a robust mesoporous hafnium (Hf)-based metal-organic framework (MOF) comprising a single-site zirconium-benzyl derivative. As a specific example, the embodiment is a compound comprising a reaction product of a hafnium-based metal-organic framework and a single-site zirconium-benzyl derivative. The Hf—ZrBn-based MOF is fully characterized through a combination of spectroscopic techniques and computational modeling. The Hf—ZrBn-based MOF is useful for catalytic activity, for example, as a single-component stereoregular polymerization catalyst for an alkene such as 1-hexene.

Figure 1:
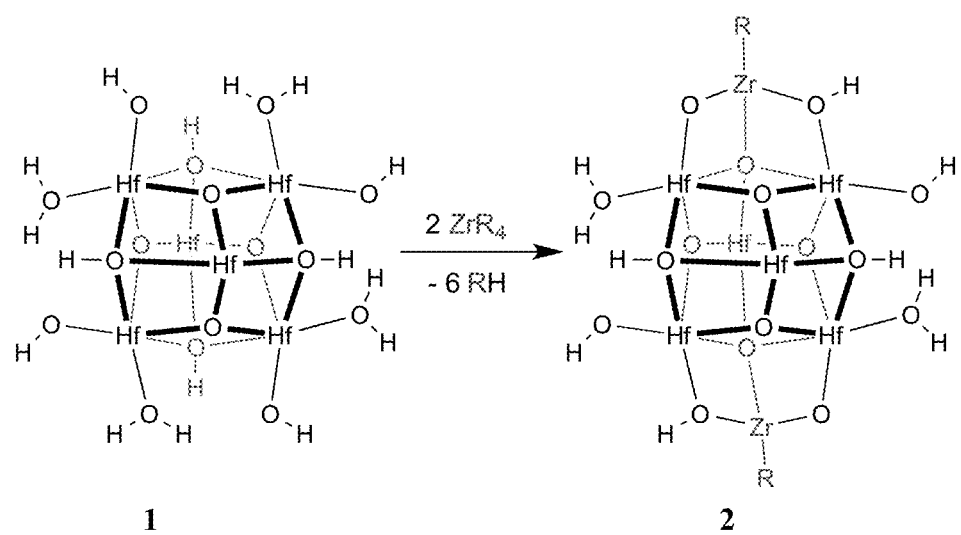
FIG. 1 is a scheme of a representative embodiment of a MOF prepared. For 2 specifically, R=benzyl.
Figure 2:
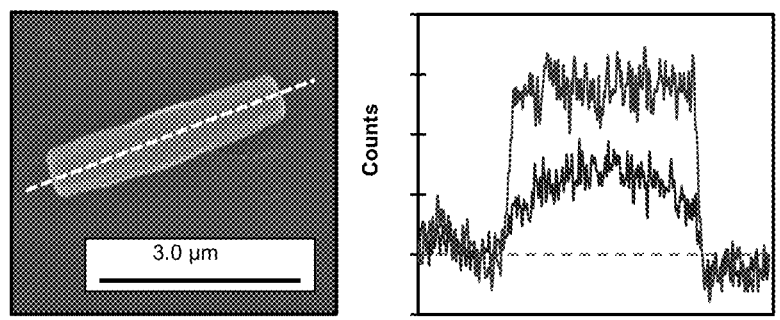
FIG. 2 provides SEM-EDX images and spectra of 2. EDX curve for Zr is the top curve and Hf is below it, while the dashed white line indicates where the EDX line scan is taken.

In a specific non-limiting example, a solution of tetrabenzylzirconium ($ZrBn_4$) in benzene is reacted with 1 ($Hf_6(OH)_{16}(TBAPy)_2$) at room temperature for 1 hour (FIG. 1). The resulting material is washed repeatedly with benzene to remove residual $ZrBn_4$, and then the benzene supernatant is exchanged with pentane to facilitate activation. The presence of Zr in the putative material 2 is investigated using inductively coupled plasma-atomic emission spectroscopy (ICP-AES). On average, approximately 2.4 Zr per $Hf_6$ node are observed. Longer exposure times or reaction at higher temperatures (50° C.) does not result in greater incorporation of Zr. In fact, greater than 1 hour exposure time produces non-uniform Zr incorporation. In addition, scanning electron microscopy-energy dispersive X-ray spectroscopy (SEM-EDX) shows uniform incorporation of Zr throughout the entire length of the MOF crystallite (FIG. 2 and FIG. 25).

The powder X-ray diffraction pattern (PXRD) of the product 2 indicates that the material maintains crystallinity after incorporation of Zr (FIG. 3). It is noted also that $N_2$ adsorption isotherms for 2 reveal that while the Brunauer-Emmett-Teller (BET) surface area decreases compared to the parent 1 material, notably, mesoporosity is maintained (FIG. 4). Table 1 shows the BET parameters and geometrical accessible surface areas from experimental 2 isotherm and parent 1 isotherm.

TABLE 1

| | $N_m$, monolayer capacity (mmol/g) | C, BET constant | BET Surface Area (m²/g) |
|---|---|---|---|
| 1 | 18.2 | 450 | 1780 |
| 2 | 11.8 | 469 | 1150 |

Figure 5:
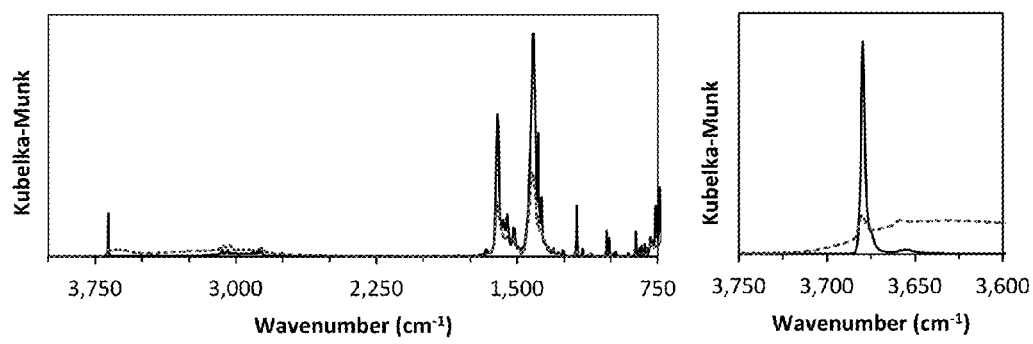
FIG. 5 shows DRIFTS spectra of 1 (solid line) and 2 (dashed line) as synthesized but exposed to air. Full spectrum (left) and —OH/—$OH_2$ region from 3600-3750 $cm^{-1}$ (right).

Diffuse reflectance infrared Fourier transform spectroscopy (DRIFTS) measurements of 2 confirm metalation of Zr by reaction with —OH and —$OH_2$ groups in the node as evidenced by a decrease in intensity of the peaks at 3678 and 3679 $cm^{-1}$ assigned to terminal —OH and —$OH_2$, respectively (FIG. 5).

Figure 6:
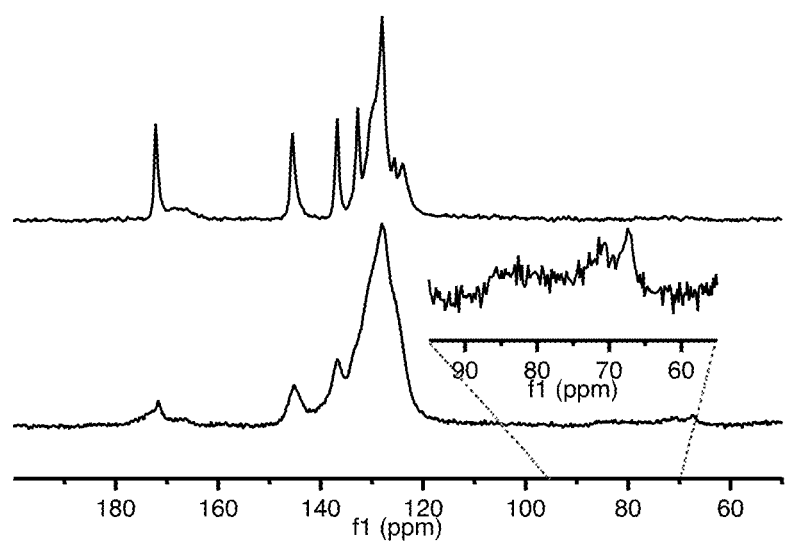
FIG. 6 is a solid-state $^{13}C$ NMR spectra of 1 (top) and 2 (bottom) and close-up of Zr—$CH_2$ region (middle).
Figure 7:
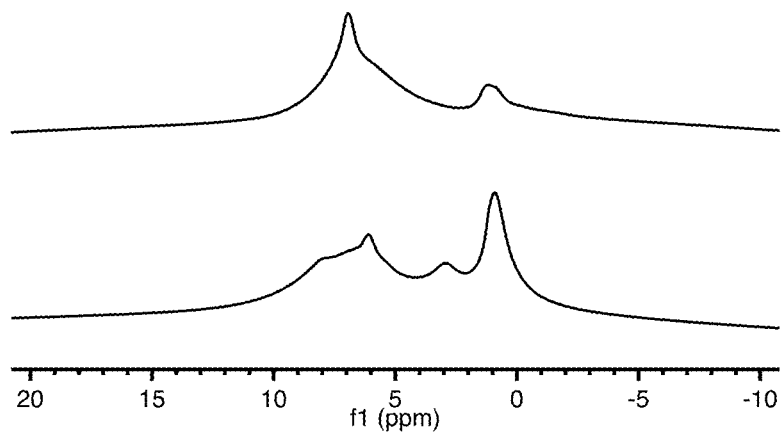
FIG. 7 is a solid-state $^1H$ NMR spectra of 1 (top) and 2 (bottom). The spectrum for 2 shows a new peak at δ 2.9 ppm, which is believed to be the Zr—$CH_2$ protons.

2 is also investigated via solid-state (SS) NMR spectroscopy. The $^{13}C$ cross-polarization-magic angle spinning (CP-MAS) spectrum of 2 contains aromatic resonances corresponding to the carbon atoms of the framework 1,3,6,8-tetrakis(p-benzoate)pyrene (TBAPy) linker-similar to the spectrum for the parent MOF 1 (Stylianou et al. reports the SS $^{13}C$ CP-MAS spectrum of a related MOF with the TBAPy ligand; see Stylianou, K. C. et al., *J. Am. Chem. Soc.* 2010, 132, 4119, incorporated herein by reference). However, the $^{13}C$ CP-MAS spectrum of 2 also contains a broad resonance centered at δ=67 ppm, which is in the chemical shift range expected for a $ZrCH_2$ carbon (FIG. 6) (Popoff, N. et al., *Chem. Eur. J.* 2013, 19, 964; Popoff, N. et al., *Eur. J. Inorg. Chem.* 2014, 2014, 888; and Rong, Y. et al., *Organometallics* 2012, 31, 8208, all incorporated herein by reference). The $^1H$ MAS spectrum of 2 likewise reveals a new peak at δ 2.9 ppm, which is tentatively assigned to $ZrCH_2$ protons (FIG. 7). Due to the broadness of the SS $^1H$ NMR spectra, it is difficult to assign this peak with complete authority. It is worth noting that Zr—$CH_2$ protons are particularly sensitive to their environment and exhibit resonances in a broad range of ppm values. The low intensity of the signal corresponding to the $ZrCH_2$ carbon precluded confirmation of NMR assignments through a 1H-13C heteronuclear NMR correlation (HETCOR) experiment. Nonetheless, these SS NMR data provide evidence for the presence of a Zr—$CH_2$Ph moiety in 2.

Figure 8:
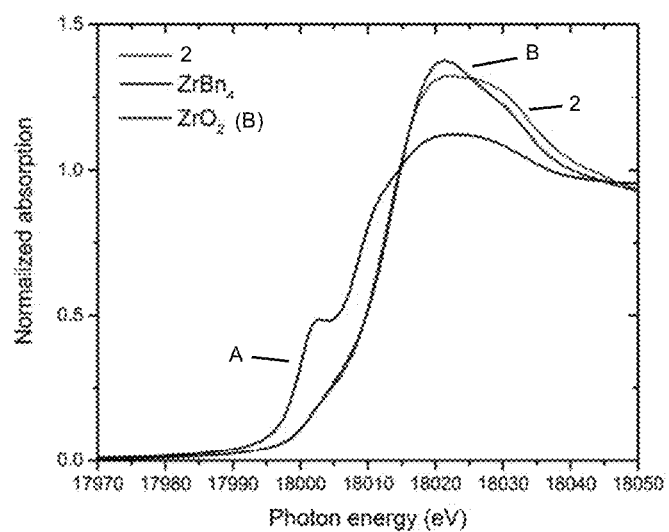
FIG. 8 provides XANES spectra of 2, $ZrBn_4$ and $ZrO_2$.

Additional information on the structure of the supported organozirconium species is obtained via X-ray absorption spectroscopy (X-Ray absorption spectroscopy, or XAS). The X-ray absorption near edge structure (XANES) Zr K-edge energy of 2 is 18001.5 eV, very similar to that of $ZrO_2$ and consistent with a Zr(IV) oxidation state (FIG. 8). Fitting the extended X-Ray absorption fined structure (EXAFS) spectrum of 2 is achieved via a different method utilizing reference compounds to determine the individual ligand scattering contributions (FIG. 9). The best fit is obtained for 1 Zr—Bn ligand and 3 Zr—O ligands. The Zr—C bond is identical to that in $Zr(Bn)_4$, 2.29 A, while the Zr—O bonds are slightly shorter than those in $ZrO_2$, 2.13 and 2.15Å, respectively.

Organozirconium precursor-MOF surface interactions are next modeled using Density Functional Theory (DFT) calculations. Investigation of the reaction of $ZrBn_4$ with 1 reveals that a Zr-monobenzyl species is the lowest energy product on the reaction pathway, that is, protonolytic release of the fourth and final benzyl ligand coming from $ZrBn_4$ (to yield a purely Zr-oxo species) is uphill energetically (SI). Zr species C is thus predicted to be in the 4+ oxidation state and 4-coordinate with three "Hf—O" ligands, originating from the MOF $Hf_6$ node, and one benzyl ligand in agreement with the model determined from EXAFS data as well as our experimental data suggesting the presence of a Zr-benzyl moiety (FIG. 10, middle).

Figure 10:
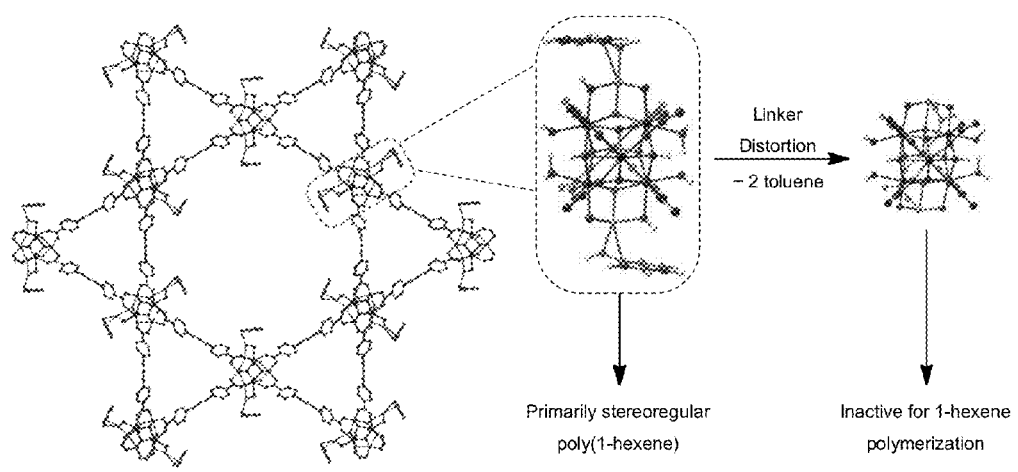
FIG. 10 are calculated crystal structures showing hexagonal pore of 2 with 2 Zr/$Hf_6$ cluster (left), close-up of Zr species C with 3 Zr—O bonds and 1 Zr—Bn bond (middle), and close-up of Zr species D2 with 4 Zr—O (right) and expected reactivity with 1-hexene.

In addition, and referring to FIG. 10, a second potential product is located resulting from a carboxylate (CO)$O^-$ group (originating from the TBAPy linker) shifting from the $Hf_6$ cluster to the Zr atom of C to form the intermediate C2. C2 is then further reacted to lose toluene and form a new product D2 with no Zr—C bond. D2 is a 4-coordinate Zr(IV) species with average Zr—O bond lengths of 1.99Å (FIG. 10, right). The EXAFS first shell coordination data is found to fit equally well with D2 with 4 Zr—O bonds at 2.15Å. While D2 is determined to be −30 kJ/mol more stable than C, SS NMR spectroscopy, as well as catalysis results (see above), suggest that at least some of the time, the Zr moiety in the MOF is best represented by species C.

Figure 11:
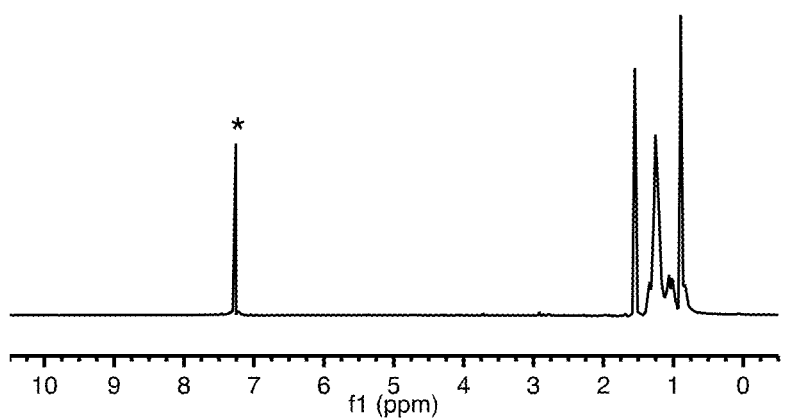
FIG. 11 is a $^1H$ NMR spectrum of poly(1-hexene) in $CDCl_3$. The residual protio impurity of $CDCl_3$ is indicated with an asterisk.
Figure 12:
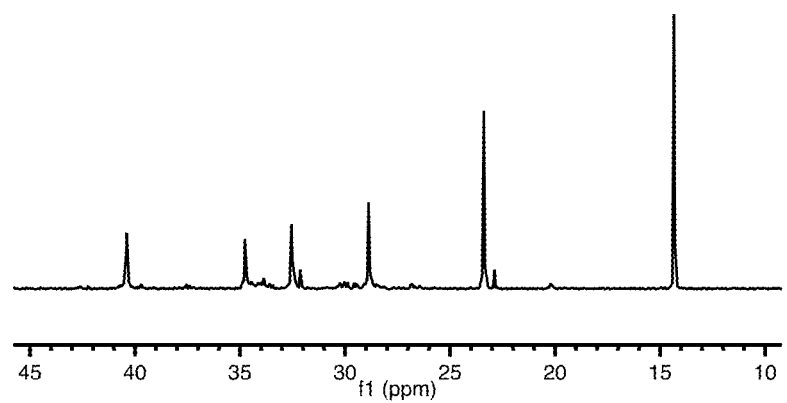
FIG. 12 is a $^{13}C$ NMR spectrum of poly(1-hexene) in $CDCl_3$ at room temperature.
Figure 13:
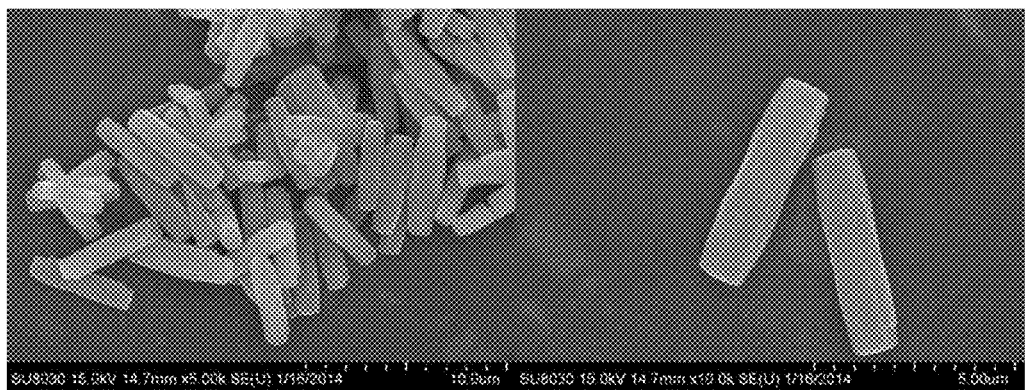
FIG. 13 are SEM images of 2 as synthesized but exposed to air.
Figure 14:
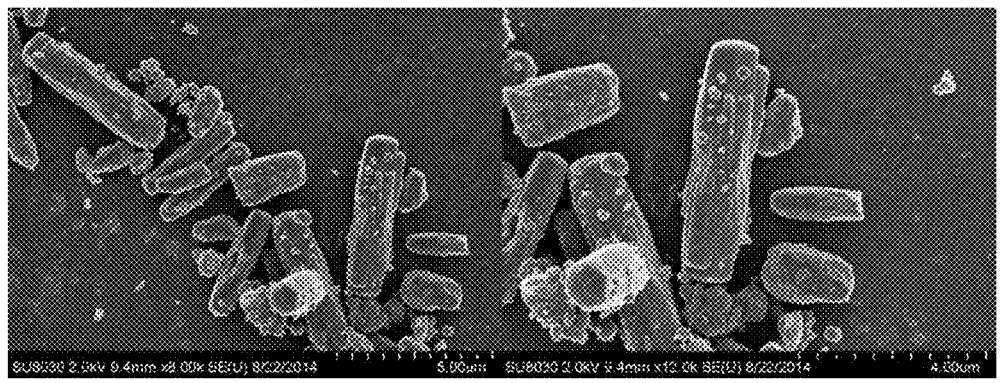
FIG. 14 are SEM images of 2 after polymerization of poly(1-hexene) with polymer extracted.
Figure 15:
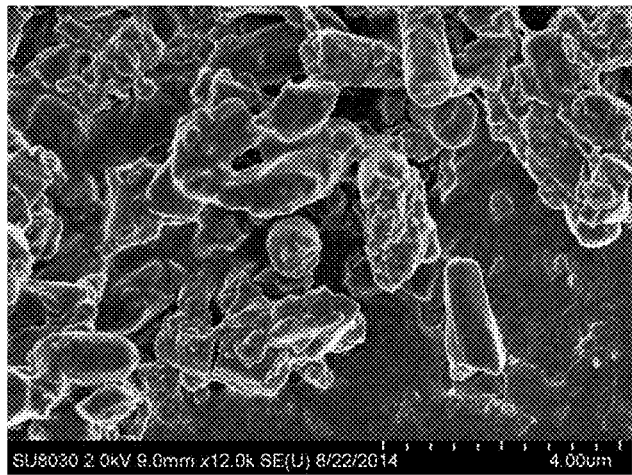
FIG. 15 are SEM images of 2 after polymerization of poly(1-hexene) without polymer extracted
Figure 16:
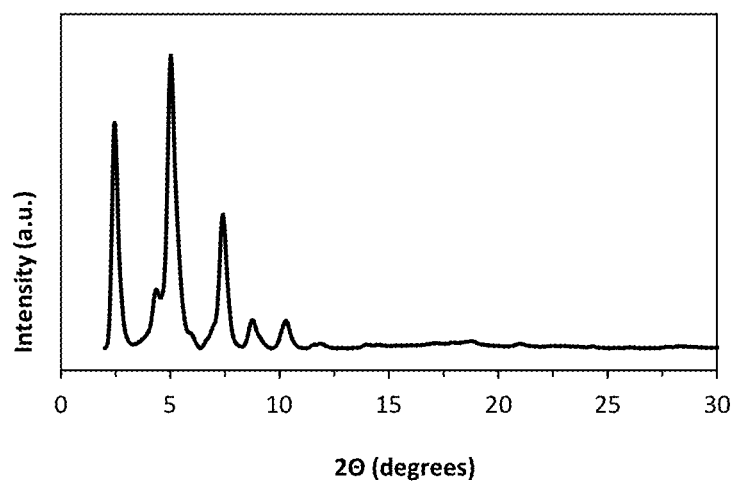
FIG. 16 is a PXRD pattern of 2 after polymerization of 1-hexene.

Zr-benzyl species are known to be catalysts for olefin polymerization, typically in the presence of an activator or co-catalyst (Chen, E. Y. -X. et al., *Chem. Rev.* 2000, 100, 1391). Addition of 2 mL of 1-hexene to 45 mg of 2 under an Ar atmosphere results in an immediate change of the viscosity of the solution (report of single component ethylene polymerization with ZrBn4 supported on $Al_2O_3$ dehydrated at 500° C. in Yermakov, Y. et al., *Adv. Catal.* 1975, 24, 173, incorporated herein by reference). After stirring the reaction for 1 hour under Ar, the supernatant is extracted and dried in vacuo. NMR spectroscopy of the resulting colorless highly viscous liquid reveals the presence of primarily stereoregular poly(1-hexene) (FIGS. 11 and 12). No polymer is observed upon addition of 1-hexene to either the parent MOF 1 or to $ZrBn_4$ under identical reaction conditions. Analysis of the MOF after polymerization by PXRD and SEM spectroscopy indicates that the MOF remains crystalline and that the MOF crystallites are primarily intact (FIGS. 13-16).

Interesting, the single-component behavior of 2 clearly indicates some cationic character of the Zr center. In fact, CM5 and natural population analysis (NPA) calculations on the catalytically active species C reveal positive electron density at the Zr metal center (Table 2), which may facilitate monomer coordination, insertion and ultimately polymerization.

TABLE 2

|  | C | C1 | C2 | $ZrBn_4$ |
|---|---|---|---|---|
| CM5 | 1.172 | 1.204 | 1.196 | 0.715 |
| NPA | 1.996 | 2.021 | 1.992 | 1.612 |

EXAMPLES

General—Air- and moisture-sensitive compounds are manipulated using standard high-vacuum and Schlenk techniques or manipulated in a glovebox under an Ar atmosphere. Toluene, and n-pentane (Sigma-Aldrich) are dried over activated alumina columns using the Grubbs method (Pangborn, A. B.; Giardello, M. A.; Grubbs, R. H.; Rosen, R. K.; Timmers, F. J. *Organometallics* 1996, 15, 1518-1520.) and are additionally vacuum-transferred from Na/K alloy prior to use (CAUTION! Na/K allow is extremely pyrophoric). Benzene and 1-hexene (Sigma-Aldrich) are distilled from Na/K alloy. Tetrabenzylzirconium is purchased from Strem Chemicals and purified via re-crystallization from cold pentane at −48° C. (Zucchini, U.; Albizzati, E.; Giannini, U. J. *Organomet. Chem.* 1971, 26, 357-372.) Hf—NU-1000 is synthesized as provided below in Example 1, according to a previously published literature procedure. (Beyzavi, M. H.; Klet, R. C.; Tussupbayev, S.; Borycz, J.; Vermeulen, N. A.; Cramer, C. J.; Stoddart, J. F.; Hupp, J. T.; Farha, O. K. *J. Am. Chem. Soc.* 2014, 136, 15861-15864, the entirety of which is incorporated herein by reference.) Deuterated chloroform ($CDCl_3$, Cambridge, 99.8%) is used as received without further purification.

Instrumentation—Inductively coupled plasma-atomic emission spectroscopy (ICP-AES) data are collected on Varian Vista MPX Spectrometer. Scanning electron microscopy (SEM) images and energy dispersive spectroscopy (EDX) profiles are collected on a Hitachi SU8030. Powder X-ray diffraction (PXRD) measurements are carried out on a Bruker MX IpS microsource with Cu Kα radiation and an Apex II CCD detector. The samples are mounted in capillaries as powders, sealed with wax and placed on a goniometer head. The data are collected on an area detector with rotation frames over 180° in ϕ and at 2θ values of 12, 24, and 36° being exposed for 10 minutes at each frame. Overlapping sections of data are matched and the resulting pattern is integrated using Bruker's APEX2 phase ID program. The powder patterns are treated for amorphous background scatter. $N_2$ adsorption isotherms are collected on a Tristar II 3020 (Micromeritics). All pore size distributions are obtained using a carbon slit pore model with a $N_2$ kernel (Micromeritics). NMR spectra are recorded on a Bruker Avance III 500 (direct cryoprobe, 500 MHz, $^1H$; 125, $^{13}C$) instrument. Chemical shifts for $^1H$ and $^{13}C$ spectra are referenced using internal solvent resonances and are reported relative to tetramethylsilane (TMS). $^{13}C$ cross-polarization-magic angle spinning (CP-MAS) solid-state (SS) NMR spectra are recorded on a Varian VNMRS 400 (FT, 100 MHz, $^{13}C$). For $^{13}C$ CP-MAS solid-state NMR spectroscopy, air-sensitive samples are loaded into cylindrical zirconia rotors in the glovebox and capped with a solid Teflon cap. Chemical shifts (δ) for $^{13}C$ CP-MAS SS NMR spectra are reported relative to the external methylene signal of adamantane (δ=38.48 ppm).

Example 1

Synthesis of 1

A) Synthesis of 1,3,6,8-tetrakis(p-benzoic acid)pyrene (TBAPy)

A mixture of (4-(methoxycarbonyl)phenyl)boronic acid (1.040 g, 5.80 mmol), 1,3,6,8-tetrabromopyrene (0.500 g, 0.97 mmol), tetrakis(triphenylphosphine) palladium(O) (0.030 g 0.026 mmol), and potassium tribasic phosphate (1.100 g, 5.30 mmol) in dry dioxane (20 mL) is loaded (in a glovebox) into a 20 mL microwave vial (Biotage) and capped. This mixture is stirred under argon for 72 hours at 130° C. in an oil bath. The reaction mixture is evaporated to dryness and the solid residue is washed with water to remove inorganic salts. The insoluble material is extracted with chloroform (three times by 50 mL), the extract is dried over magnesium sulfate, and the solvent volume is reduced under vacuum. The residue is boiled in tetrahydrofuran for 2 hours and filtered, the resulting filtrate containing mainly impurities. This procedure gives 0.58 g of 1,3,6,8-tetrakis(4-(methoxycarbonyl)phenyl)pyrene (82% yield). 1H NMR (CDCb-d): δ 3.99(s, 12H), 7.75 (d, 8H), 8.01 (s, 2H), 8.15 (s, 4H), 8.23 (d, 8H).

B) Synthesis of 1,3,6,8-tetrakis(p-benzoic acid)pyrene ($H_4TBAPy$)

To a 250 mL round bottom flask containing 0.58 g (0.78 mmol) of solid 1,3,6,8-tetrakis(4-(methoxycarbonyl)phenyl) pyrene, a solution containing 1.5 g (3 7.5 mmol) NaOH in 100 mL of a THF/water (ratio 1:1) mixture is added and the resultant suspension is vigorously stirred under reflux overnight. The solvents are removed under vacuum and water is added to the residue, which forms a clear yellow solution. The clear yellow solution is stirred at room temperature for 2 hours and the pH value is adjusted to 1 using concentrated HCl. The resulting yellow solid is collected by filtration and washed with water several times. The crude product is recrystallized from DMF, filtered, washed with chloroform and dried under vacuum. This affords 0.49 g (91%) of the pure product H$_4$TBAPy. 1H NMR (DMSO-d6): δ7.86 (d, 8H), 8.09 (s, 2H), 8.17 (d, 8H), 8.21 (s, 4H), 13.12 (s, 4H).

C) Synthesis of 1

500 mg of HfOCl$_2$·8 H$_2$O (1.22 mmol), 10.80 g (88.4 mmol) of benzoic acid and 32 mL of DMF are added to a 100 mL media bottle and the solids are dissolved via sonication. The resulting cloudy solution is incubated in an oven at 80° C. for 1 hour, then removed from the oven and cooled to room temperature. 160 mg (234 mmol) of H$_4$TBAPy is then added to the reaction solution and the mixture is sonicated for 10 minutes to yield a yellow suspension. The reaction mixture is placed in a 100° C. oven for 24 hours, during which time yellow powder precipitates from the solution. After 24 hours, the reaction is removed from the oven and cooled to room temperature. The solid is isolated by centrifugation, washed three times with 25 mL of DMF through repeated centrifugation and re-dispersion and then soaked in 40 mL of DMF for 8 hours. Subsequently, the yellow solid is isolated by centrifugation and re-suspended in 25 mL of DMF, transferred back into a 100 mL media bottle and 2.0 mL of 8 M aq. HCl is added. The reaction mixture is incubated in a 100 ° C. oven for 18 hours and then removed from the oven and cooled to room temperature. The solid is isolated by centrifugation, washed three times with 25 mL of DMF, washed three times with 40 mL of acetone, and soaked in 40 mL of acetone for 18 hours. The solid is activated at 120° C. under vacuum for 18 hours. Yield: 232 mg (73% yield). Elemental analysis calculated for 1, Hf$_6$(OH)$_{16}$(TBAPy)$_2$ (%): C, 39.14; H, 2.24; Hf, 39.66. Found (1) : C, 39.97; H, 1.93; Hf, 34.9. (2) C, 40.02; H, 1.88; Hf, 34.9.

Example 2

Synthesis of 2

In an Argon glovebox, five 40.0 mg samples of 1 are weighed out in 20-mL vials and a 0.5 mL portion of dry benzene is added to each vial via syringe. To a new 20 mL vial is added 137.5 mg of ZrBn$_4$, then 6.5 mL of benzene is added by syringe to make a homogeneous yellow solution. A 1.3 mL portion of the ZrBn$_4$ solution is then added dropwise to each vial of 1 with swirling to mix the solution. Upon addition of ZrBn$_4$, the MOF immediately turns from yellow to orange. After 1 hour, the supernatant is carefully removed from each vial by pipet and 1.5 mL of fresh benzene is added to the reaction solution with swirling. After 10 minutes, the benzene supernatant is again washed with fresh benzene. After exchanging the benzene supernatant 4×1.5 mL, the supernatant is observed to be colorless. The supernatant is then exchanged 2×2mL with dry pentane and the MOF is left soaking in the pentane solution for 18 hours at room temperature. The following day, the pentane supernatant is removed by pipet and the MOF powder from each of the 5 vials is then combined into one batch. Residual solvent from the combined batch of 2 is then removed in vacuo at room temperature to yield approximately 200 mg of yellow powder. Longer exposure times or reaction at higher temperature does not increase incorporation of Zr into 1, as evidenced in Table 3.

TABLE 3

| Exposure Time | Zr/Hf$_6$ |
| --- | --- |
| 1 | 2.4 |
| 3 | 2.8 |
| 5 | 2.6 |

TABLE 3-continued

| Exposure Time | Zr/Hf$_6$ |
| --- | --- |
| 24 | 2.6 |
| 24 (50° C.) | 2.5 |

Example 3

ICP-AES Analysis

Approximately 2 mg of sample 2 is added to a microwave vial (4 mL) and a 1.0 mL solution of 1:3 v/v 30% H$_2$O$_2$/conc. H$_2$SO$_4$ is added. The vial is capped and irradiated in a microwave oven at 150° C. for 5 min. The resulting clear solution is diluted to 25 mL with nanopure water and analyzed via ICP-AES. Zr and Hf concentrations are calculated from external stock solutions to determine the relative ratio of each element in 2.

Example 4

X-ray Absorption Spectroscopy (XAS) Measurements

Zr K-edge (17998 eV) EXAFS and XANES data are collected on the bending magnet beam line of the Materials Research Collaborative Access Team (MRCAT, Sector 10) at the Advanced Photon Source, Argonne National Laboratory. The beamline is detuned to 50% in order to minimize the presence of harmonics. Data are taken in step scan mode with data points of 0.3 eV in the XANES region and 0.07 Å$^{-1}$ in the EXAFS region. Complete XANES and EXAFS spectra are obtained in about 10 minutes under N$_2$ at 25° C. Measurements are made in the transmission mode with the ionization chambers optimized for the maximum current with linear response (~10$^{10}$ photons detected s$^{-1}$) using gas mixtures (75% N$_2$+25% Ar) to give 10% absorption in the incident X-ray detector and 35% absorption (Ar) in the transmission X-ray detector. A Zr foil spectrum is acquired simultaneously with each measurement for energy calibration. Catalyst samples are pressed into a cylindrical holder of ca. 5 mm diameter with a thickness chosen to give a total absorbance (μx) of about 2.0.

Example 5

X-Ray Absorption Fine Structure Spectroscopy Data Analysis

Standard analysis is performed using WinXAS 3.1 software (Ressler, T., *J. Synchrot. Radiat.* 1998, 5, 118-122, incorporated herein by reference). The absorption spectra are normalized using a linear polynomial for the pre-edge region and a third-order polynomial for the post edge region. The background subtraction is performed using a cubic spline with 5 nodes from about 2 to 12Å$^{-1}$. The edge energy is determined from the maximum in the first peak of the first derivative of the XANES. Several models are evaluated to determine the first shell Zr coordination. Initially, local structure is assumed to be Zr—O at an identical bond distance. Since the surface Zr structure potentially contains both Zr—O bonds to the Hf and Zr—C bonds from remaining Zr-benzyl ligands, fitting is also done by taking chi for 2 and subtracting chi for scattering from different numbers of Zr—Bn bonds and fitting the remaining EXAFS with Zr—O bonds. The scattering for a single Zr—Bn ligand is obtained by dividing chi for Zr(Bn)$_4$ by 4. The difference EXAFS, i.e., 2—x Zr—Bn, is fit. Experimental Zr—O phase shift and backscattering amplitudes are determined from the reference compound Zr(IV) acetyleacetate (8 Zr—O at 2.19 Å). The EXAFS parameters are obtained by a least square fit in R-space of the k$^2$-weighted Fourier transform (FT) data, $\Delta k=2.7–10.9$ Å$^{-1}$; while fits are performed over the range, $\Delta R=1.1–1.9$ Å. The best fit values for $\Delta\sigma^2$ is determined from a fit in k-space of the k$^2$-weighted chi of isolated first shell Zr—O coordination. The EXAFS and XANES fits are given in Table 4. In Table 4, summary of the XANES and fitted EXAFS data including the scattering path, coordination number (N), distance to the neighboring atom (R), mean-square relative displacement ($\Delta\sigma^2$), and energy shift ($\Delta E_0$). The fit method and the quality of fit are shown in FIG. 9.

TABLE 4

| Sample | Edge Energy, eV | Oxidation State | Scattering Pair | N | R, Å | afs$\Delta\sigma^2$ (×10$^3$), Å$^2$ | E$_0$, eV |
|---|---|---|---|---|---|---|---|
| Zr(Bn)$_4$ Standard | 18000.0 | +4 | Zr—O | 3.9 | 2.29 | Zr—Bn Reference | |
| Zr(AcAc)$_4$ Standard | 18001.4 | +4 | Zr—O | 8 | 2.19 | Zr—O Reference | |
| Zr(OH)$_4$ Standard | 18001.5 | +4 | Zr—O | 6.1 | 2.15 | 3.0 | −0.5 |
| ZrO$_2$ Standard | 18001.6 | +4 | Zr—O | 6.0 | 2.15 | 3.0 | −0.3 |
| 2 | 18001.5 | +4 | Zr—C (Bz) | 1.0 | 2.29 | 0.0 | 1.1 |
| | | | Zr—O | 3.2 | 2.13 | 0.0 | 0.3 |
| Alternate fit | | | Zr—O only | 4.0 | 2.15 | 2.0 | 1.0 |

Example 6

Computational Details

Periodic structures for 2 are optimized with periodic density functional theory (DFT). The ZrBn groups were placed only on the central node of 1 primitive cell, which contains three Hf$_6$-nodes. There is very little linker distortion in the ZrBn structures, indicating that each node in 1 is isolated. The generalized gradient approximation (GGA) is used, exchange-correlation functional PBE as implemented in the Vienna Ab Initio Simulation Package (VASP) (Perdew, J. P. et al., *Phys. Rev. B* 1992, 45, 13244-13249; Perdew, J. P. et al., *Phys. Rev. Lett.* 1996, 77, 3865-3868; Perdew, J. P. et al., *J. Chem. Phys.* 1996, 105, 9982-9985; Kresse, G. et al., *Phys. Rev. B* 1996, 54, 11169-11186; Kresse, G. et al., *Phys. Rev. B* 1994, 49, 14251-14269; Kresse, G. et al., *Phys. Rev. B* 1993, 47, 558-561; and Kresse, G. et al., *Comput. Mater. Sci.* 1996, 6, 15-50, all incorporated herein by reference). VASP calculations used projector-augemented wave potentials to describe the interaction between core and valence electrons. A plane-wave kinetic energy cutoff of 520 eV is used. The optimizations are each performed with a single k-point, and the energy and force optimization thresholds are 10$^{-5}$ eV and 0.05 eV Å$^{-1}$, respectively.

All cluster calculations are performed with the M06-L density functional as implemented in the Gaussian 09 software (Zhao, Y. et al., *J. Chem. Phys.* 2006, 125, 194101 and Frisch, M. J et al., Gaussian 09, revisions B.01 and A.02; Gaussian, Inc.: Wallingford, Conn., 2009, both incorporated herein by reference). The def2-SVP split-valence basis set is used for H, C, N, O and Hf atoms in conjunction with the def2-ECP pseudopotential for Zr and Hf (Weigend, F. et al., *Phys. Chem. Chem. Phys.*, 2005, 7, 3297, incorporated herein by reference). An automatic density-fitting set generated by the Gaussian program is used to reduce the cost for calculations done with the local density functional M06-L. Natural population analysis is performed using the NBO program implemented in the Gaussian program. CM5 charges are calculated employing the CM5PAC software (NBO Version 3.1, Glendening, E. D. et al. and Marenich, A. V. et al., *J. Chem. Theor. Comput.* 2012, 8, 527-541, both incorporated herein by reference).

Figure 17:
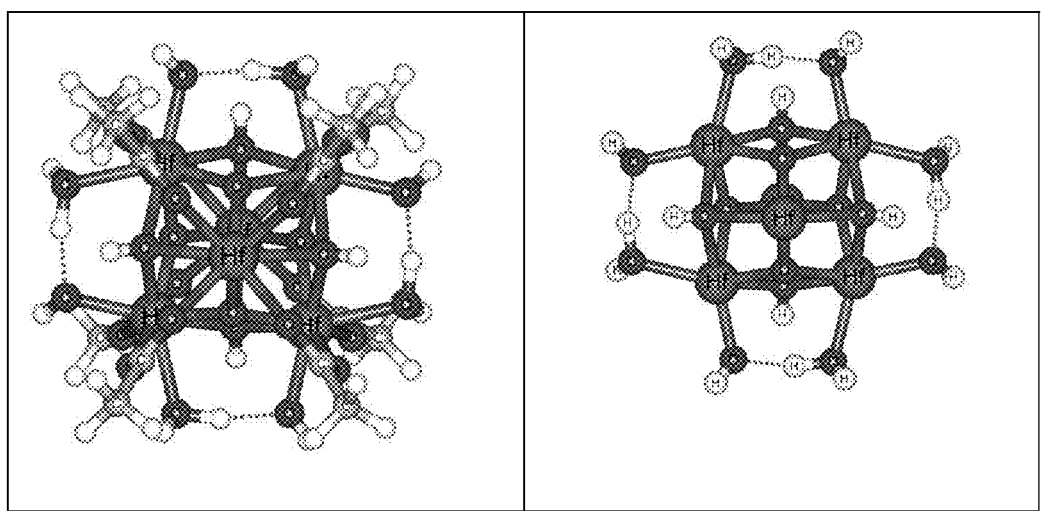
FIG. 17 is a model cluster of the $Hf_6$-node (left) and the $Hf_6$-node without MeCOO— linkers.

The cluster model of the Hf$_6$-node employed in this work is [Hf$_6$($\mu_3$—O)$_4$($\mu_3$—OH)$_4$(OH)$_4$(H$_2$O)$_4$(MeCOO)$_8$], where the original TBAPy$^{4-}$ ligands (1,3,6,8-tetrakis(p-benzoate) pyrene) are replaced by 4 acetate-anions (FIG. 17).

Calibration calculations are carried out to see how two methods predict a difference in energy for similar structures. Products C and C2 (FIG. 18) are used for these calculations. VASP single point calculations are performed in a large box with sides 50×50×50 Å$^3$ to mimic cluster calculations. Gaussian calculations (M06-L/def2-SVP) predict the energy difference of −41 kJ/mol, while VASP (PBE/plane waves) gives −49.3 kJ/mol. Thus, two methods are consistent with each other in predicting the more stable structure, though energy difference between two methods can go to 8 kJ/mol.

Example 7

Computational Study of the Mechanism of Formation of 2

Figure 19:
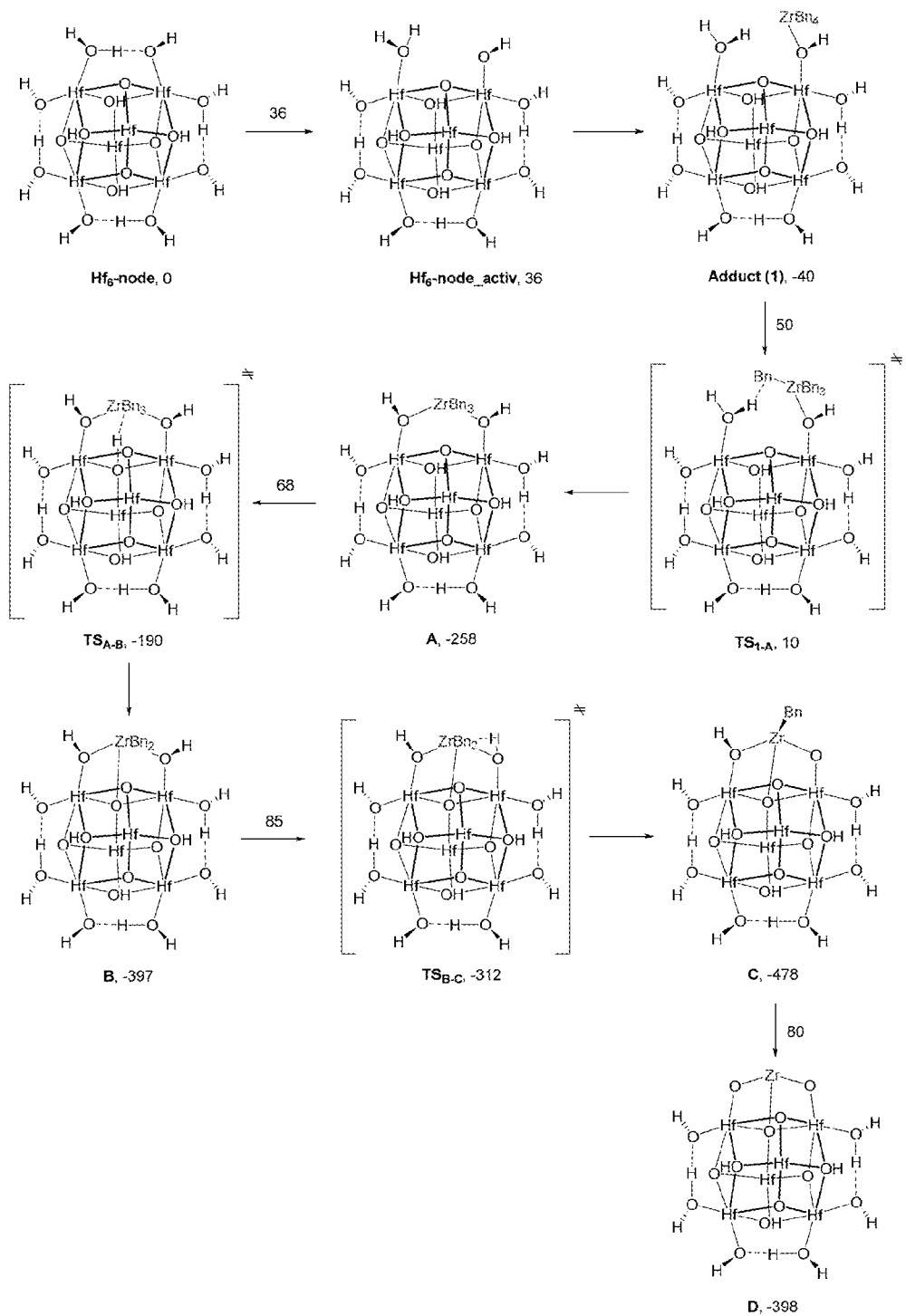
FIG. 19 is a mechanistic scenario of the reaction between the $Hf_6$-node and $ZrBn_4$. Numbers are Gibbs free energies in kJ/mol.
Figure 20:
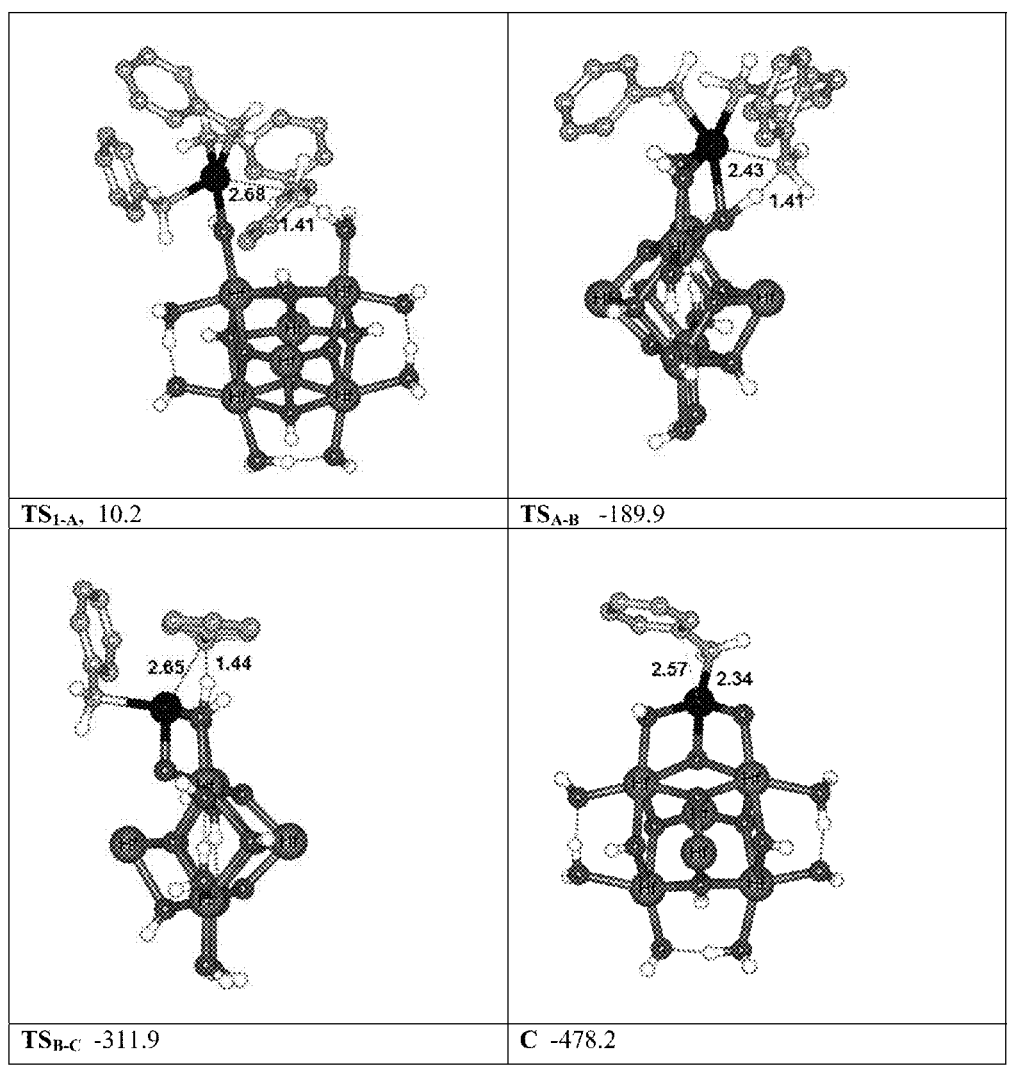
FIG. 20 provides optimized geometries of the transition states $TS_{1-A}$, $TS_{A-B}$, $TS_{B-C}$ and the product C. Numbers are Gibbs free energies in kJ/mol.

The initial step of the reaction is the formation of an adduct 3 upon binding of ZrBn$_4$ by Hf$_6$-node (FIG. 19). Binding occurs to the terminal OH upon rupture of the central H-bond. The H-bond breaking is endoergic by 36 kJ/mol, while the following adduct formation is exoergic by 76 kJ/mol. In the next step, a H atom of the aqua ligand inserts into the C—H bond of benzyl ligand of ZrBn$_4$. The insertion occurs via TS$_{1-A}$ (FIG. 20) and yields intermediate A and a free toluene. This step is highly exoergic ($\Delta G°_{298}=-268$ kJ/mol), while the free energy barrier is a moderate one ($\Delta G^{\neq}=50$ kJ/mol). In the next step, the insertion takes place intramoleculariy in A via TS$_{A-B}$: H atom of the bridging $\mu_3$—OH is transferred to the benzyl group of ZrBn$_3$-moiety. The formation of the intermediate B is also an exoergic process ($\Delta G°_{298}=-139$ kJ/mol), which proceeds with a moderate barrier of 68 kJ/mol. The third insertion involves the transfer of H atom of the terminal OH to the benzyl group in B to yield C through the transition state TS$_{B-C}$ (FIG. 20). This transformation has a slightly higher barrier of 85 kJ/mol and is less exoergic ($\Delta G°_{298}=-81$ kJ/mol). The last intramolecular insertion step yielding intermediate D turns out to be endoergic by 80 kJ/mol and therefore is rejected. Thus, theory predicts that the final product of the reaction between Hf$_6$-node and ZrBn$_4$ is the monobenzyl zirconium species C. It is believed that the reaction with the second ZrBn$_4$ at the opposite site of the Hf$_6$-node occurs in a similar fashion, i.e. these processes are independent.

Figure 18:
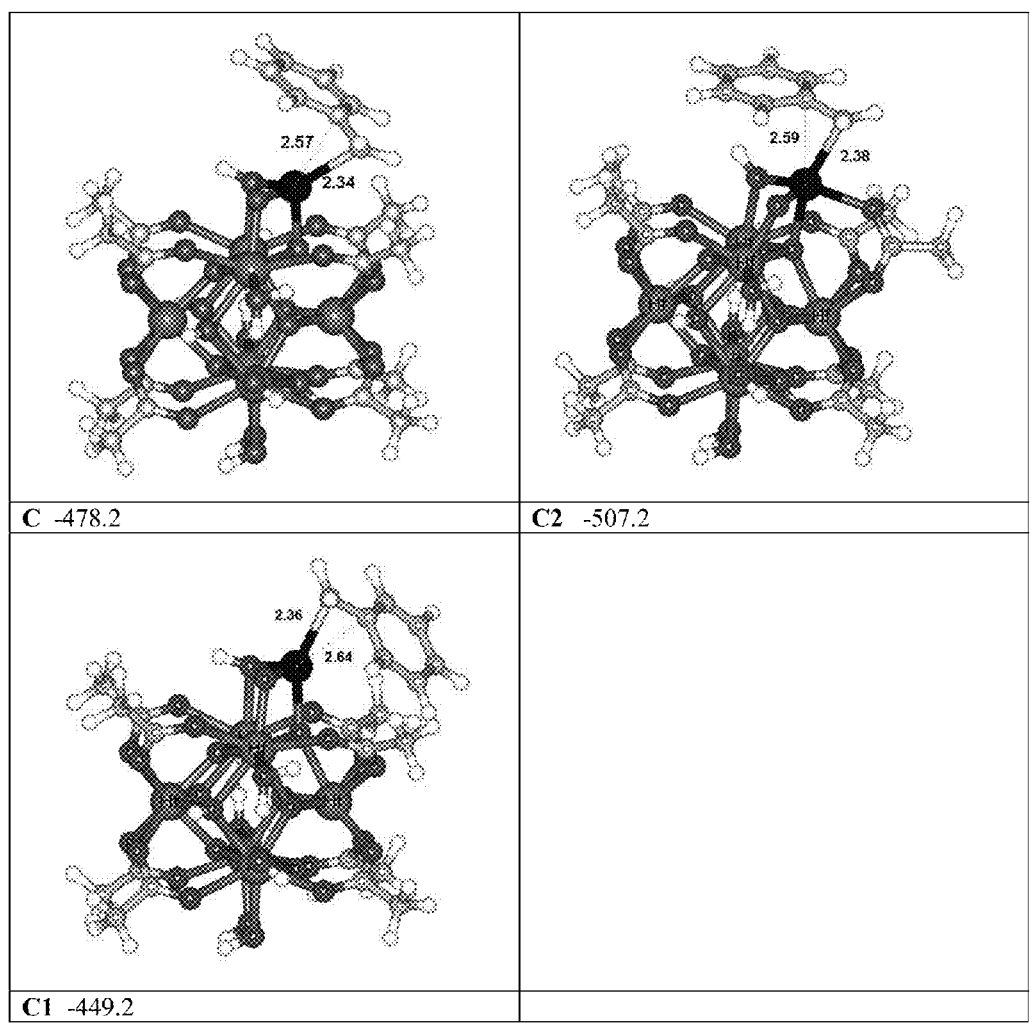
FIG. 18 provides optimized geometries of the isomers of the monobenzyl zirconium species: C, C1 and C2. Numbers are Gibbs free energies in kJ/mol.
Figure 21:
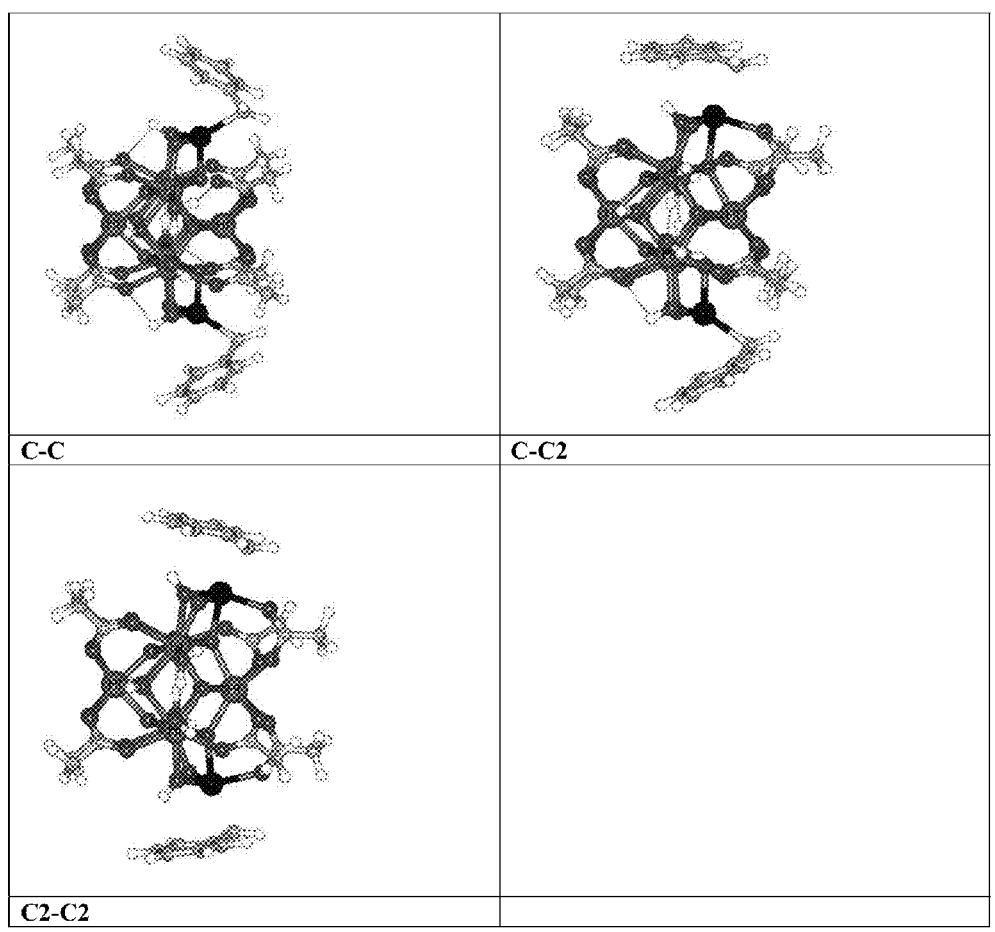
FIG. 21 provides optimized geometries of the isomers of the monobenzyl zirconium species: C-C, C-C2 and C2-C2.

Product C has two isomers C1 and C2 (FIG. 18). C1 is obtained by the rotation of the benzyl ligand along Zr—C bond and the following geometry optimization. It is less stable than C ($\Delta\Delta G°_{298}=+29$ kJ/mol). On the other hand, C2 is obtained as a result of linker recoordination from Hf to a coordinatively less saturated Zr and C2 is more stable than C ($\Delta\Delta G°_{298}$=−29 kJ/mol). Periodic DFT calculations are performed in order to test the effect of the linker rearrangement in the MOF. Cluster calculations are also done for comparison, the results are shown in Table 5 and FIG. 21. Periodic calculations consistently predict the difference in energy between isomers to be 20 kJ/mol smaller. Several factors can contribute to this difference: the model system used in cluster calculations; difference in methods used, though it is estimated to be about 8 kJ/mol in the calibration calculations; and linker rearrangement energy in the MOF, since it can do so freely in the cluster model. Taking all this into account, it is roughly estimated that the linker rearrangement energy to be ~10 kJ/mol. Thus, Gibbs free energy difference between C and C2 can be roughly estimated to be about −10 kJ/mol, if this difference is taken into account between periodic and cluster approaches. Correspondingly, the free energy difference between structures C-C and C2-C2 with two ZrBn per node is about −40 kJ/mol. Table 6 shows the relative electronic energies, enthalpies and Gibbs free energies of the reactants, intermediates and products in kJ/mol.

Table 7 shows frontier orbital (HOMO and LUMO) energies and the energy difference between them in eV.

TABLE 5

|  | Periodic | Cluster |
| --- | --- | --- |
| C-C | 0.0 | 0.0 |
| C-C2 | −23.4 | −43.0 |
| C2-C2 (both sites) | −66.4 | −89.6 |

TABLE 6

|  | $\Delta E$ | $\Delta H°_{298}$ | $\Delta G°_{298}$ | $\Delta\Delta E$ | $\Delta\Delta H°_{298}$ | $\Delta\Delta G°_{298}$ |
| --- | --- | --- | --- | --- | --- | --- |
| $Hf_6$-node | 0 | 0 | 0 | 0 | 0 | 0 |
| $Hf_6$-node activ. | 46.1 | 47.2 | 35.7 | 46 | 47 | 36 |
| Adduct 3 | −108.6 | −103.3 | −40.2 |  |  |  |
| $TS_{1-A}$ | −49.3 | −56.6 | 10.2 | 59 | 47 | 50 |
| A | −266.0 | −262.8 | −257.5 |  |  |  |
| $TS_{A-B}$ | −193.2 | −204.4 | −189.9 | 73 | 58 | 68 |
| B | −331.8 | −335.7 | −396.8 |  |  |  |
| $TS_{B-C}$ | −242.6 | −255.2 | −311.9 | 89 | 80 | 85 |
| C | −349.7 | −351.6 | −478.2 |  |  |  |
| C1 | −330.0 | −336.0 | −449.2 |  |  |  |
| C2 | −390.8 | −399.7 | −507.2 |  |  |  |
| $TS_{C2-C2'}$ | −315.1 | −322.1 | −439.7 |  |  |  |
| C2' | −347.3 | −351.8 | −474.5 |  |  |  |
| D | −206.5 | −209.6 | −397.9 |  |  |  |
| D2 | −317.6 | −323.2 | −509.3 |  |  |  |
| E | −358.3 | −353.6 | −428.4 |  |  |  |
| E2 | −398.4 | −400.8 | −483.6 |  |  |  |
| $TS_{E-F}$ | −322.9 | −320.7 | −386.8 |  |  |  |
| $TS_{E2-F2}$ | −340.9 | −345.5 | −411.0 |  |  |  |
| F | −419.8 | −412.5 | −483.2 |  |  |  |
| F2 | −473.0 | −468.4 | −538.0 |  |  |  |

TABLE 7

|  | C | C1 | C2 | $ZrBn_4$ |
| --- | --- | --- | --- | --- |
| HOMO | −5.18 | −4.94 | −4.76 | −4.78 |
| LUMO | −1.63 | −1.63 | −1.56 | −2.20 |
| gap | 3.55 | 3.31 | 3.20 | 2.58 |

Figure 22:
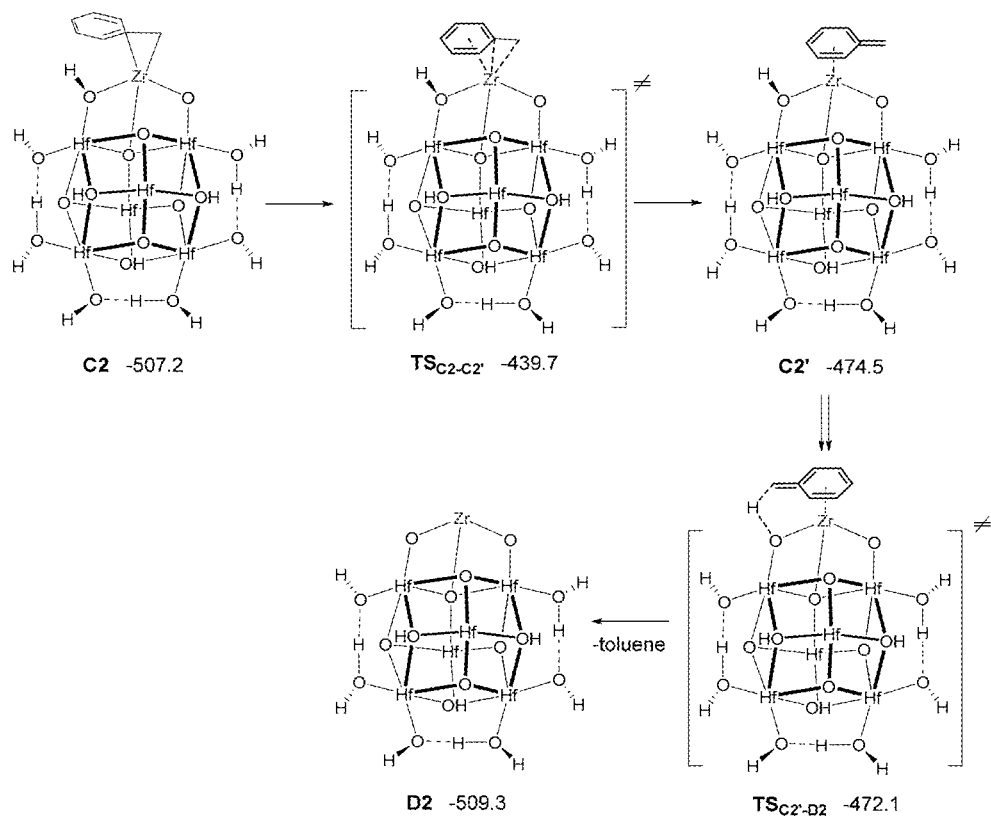
FIG. 22 is a mechanistic scenario of the release of toluene from the monobenzyl intermediate C2. Numbers are Gibbs free energies in kJ/mol.

C2 isomerizez into the corresponding higher in energy isomer C2' (FIG. 22) and form benzyl-free species D2 upon release of toluene. It is noteworthy that the isomer C2' with Bn bound to Zr via n-bonding is only possible for C2, since optimization of the analogous structure C' gives the initial C. This is easily explained by the presence of the stabilizing Zr—O (linker) bond in C2' (FIG. 18), which is absent in C'. The rate-limiting step of the transformation of C2 into D2 is the isomerization step with a moderate free energy barrier of 67 kJ/mol.

D2 is comparable in stability to the corresponding monobenzyl species C2. On the other hand, the release of toluene is an irreversible process and, therefore, if the linker rearrangement takes place in the MOF, it will mostly give the product D2.

Example 8

1-Hexene Polymerization with 2

In an Argon glovebox, to a 75-mL round bottom charged with a stirbar is added 45 mg of 2 followed by 2.0 mL of dry 1-hexene via syringe. Upon addition of 1-hexene, the solution is observed to become immediately viscous. The flask is sealed, removed from the glovebox, and stirred at room temperature for 1 hour. After 1 hour, the flask is exposed to air and approximately 10 mL of n-hexanes is added to the reaction mixture. The reaction mixture is then centrifuged to separate the supernatant and the MOF and then polymer trapped inside the MOF is further extracted with 3×10 mL n-hexanes aided by sonication. The hexane and 1-hexene extractions are combined, filtered through a syringe filter to remove any residual MOF crystallites, and then the solvent is removed in vacuo to yield a colorless highly viscous liquid determined to be poly(1-hexene). The yield of the reaction varies widely between different batches of 2 from approximately 2 mg (nearly no polymer) up to 35 mg. NMR spectroscopy of the resulting colorless highly viscous liquid reveals the presence of primarily stereo-regular poly(1-hexene) (FIGS. 11 and 12). It is believed that competition between the active polymerization species C and the unreactive species D2 explains these inconsistent results.

Example 9

Computational Study of the Mechanism of 1-Hexene Polymerization with 2

Figure 23:
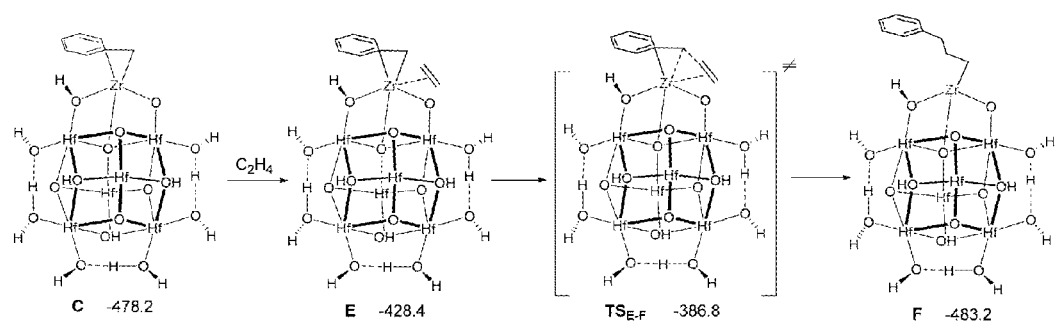
FIG. 23 is a scheme of the alkene polymerization reaction catalyzed by the monobenzyl species C. Numbers are Gibbs free energies in kJ/mol.
Figure 24:
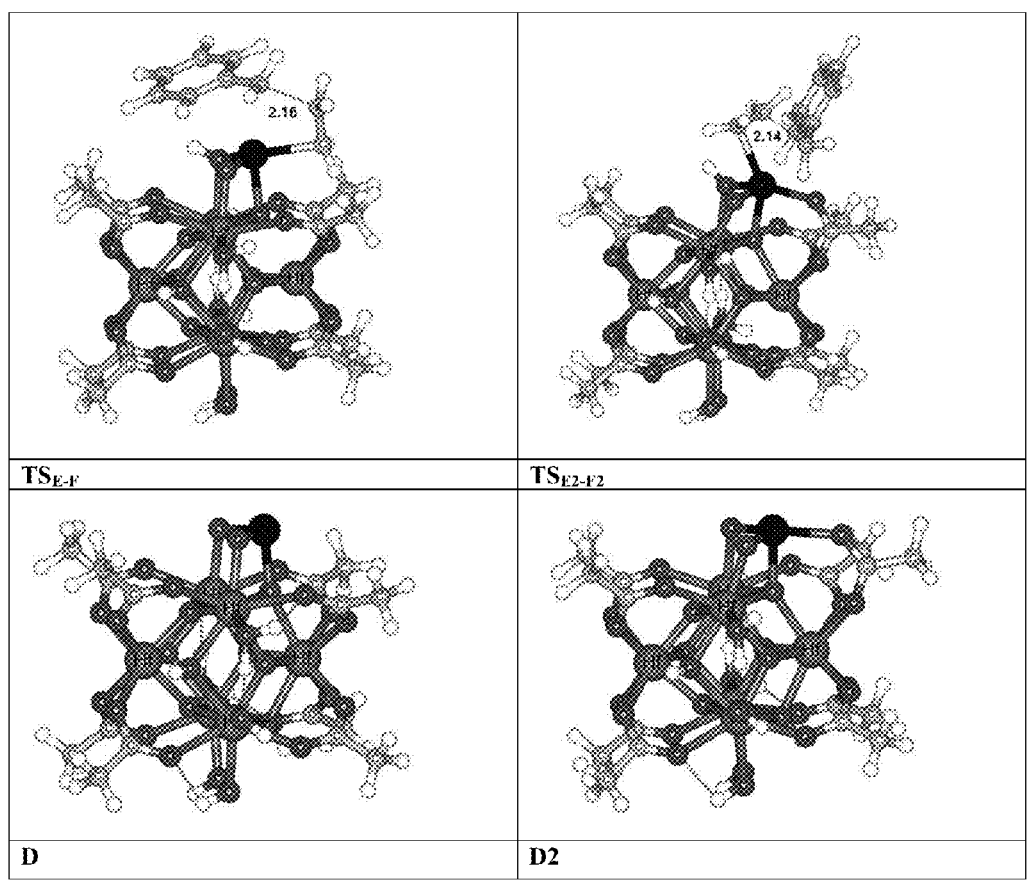
FIG. 24 provides optimized geometries of the transition states, intermediates and products: $TS_{E\text{-}F}$, $TS_{E2\text{-}F2}$, D and D2.
Figure 25A:
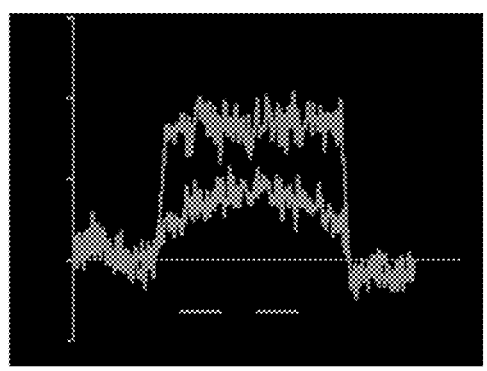
FIGS. 25A-D show SEM-EDX images of 2, wherein EDX curve for Zr is the top curve and Hf is below for A) 1 hour of $ZrBn_4$ exposure time; B) 3 hours of $ZrBn_4$ exposure time; C) 5 hours of $ZrBn_4$ exposure time; and D) 24 hours of $ZrBn_4$ exposure time.
Figure 25B:
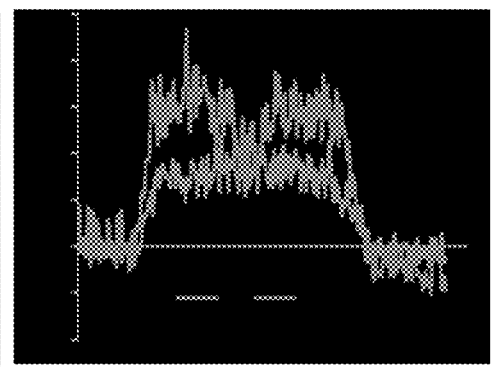
Figure 25C:
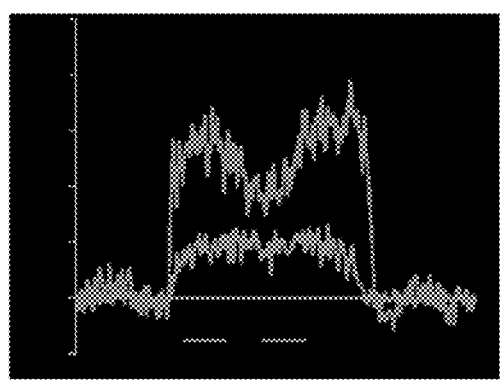
Figure 25D:
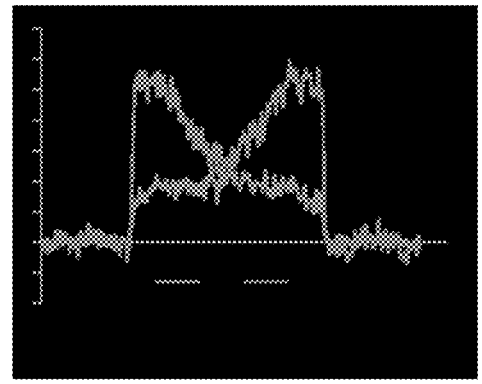

As shown above, the reaction between $Hf_6$-node and $ZrBn_4$ gives two main products C and D2. The initial steps of the alkene polymerization reaction catalyzed by C are shown in FIG. 23. The monobenzyl species C binds the incoming alkene and further undergoes C—C coupling to give intermediate F. The rate-limiting step is the C—C coupling step with a free energy barrier of 91 kJ/mol, calculated as a difference of free energies of C and $TS_{E-F}$. Thus, DFT calculations predict that the initial steps of the alkene polymerization in 2 should occur with moderate free energy barriers (below 100 kJ/mol).

D2, on the other hand, is not expected to have any polymerization activity. This result is significant because it explains why polymerization is observed to be inconsistent; i.e. not every batch of material yielded polymer.

In light of the foregoing, it is concluded that the main products of the reaction between $ZrBn_4$ and $Hf_6$-node are monobenzyl species C (regular) and D2 (with linker rearrangement).

In conclusion, an organozirconium species is synthesized and characterized by supporting a homogeneous complex onto a periodic MOF platform. This complex is demonstrated to be a promising active single-component catalyst for olefin polymerization.

The disclosures of all articles and references, including patents, are incorporated herein by reference. The invention and the manner and process of making and using it are now described in such full, clear, concise and exact terms as to enable any person skilled in the art to which it pertains, to make and use the same. All references cited in this specification are incorporated herein by reference. It is to be understood that the foregoing describes preferred embodiments of the present invention and that modifications may be made therein without departing from the spirit or scope of the present invention.

What is claimed is:

1. A compound comprising a reaction product of a hafnium-based metal-organic framework and a single-site zirconium-benzyl derivative.

2. The compound of claim 1 wherein the hafnium-based metal-organic framework has an organic portion comprising 1,3,6,8-tetrakis(p-benzoate)pyrene (TBAPy).

3. The compound of claim 2 wherein the single-site zirconium-benzyl derivative is tetrabenzylzirconium (ZrBn$_4$).

4. The compound of claim 3 wherein the hafnium-based metal-organic framework has a formula Hf$_6$(OH)$_{16}$(TBAPy)$_2$.

5. The compound of claim 4 wherein the compound has on average 2.4 Zr per Hf$_6$.

6. The compound of claim 4 wherein the compound has three Zr—O bonds and one Zr—Bn bonds.

7. The compound of claim 1 wherein the compound is crystalline.

8. A method of using a metal-organic framework for alkene polymerization, the method comprising:
providing a compound of claim 1;
contacting the compound with an alkene under at least one of a pressure and temperature sufficient to polymerize the alkene.

9. The method of claim 8 wherein the alkene is 1-hexene.

10. The method of claim 8 wherein the compound remains crystalline after the alkene is polymerized.

11. The method of claim 9 wherein the polymerized 1-hexene is stereoregular.

12. The method of claim 8 wherein the hafnium-based metal-organic framework has an organic portion comprising 1,3,6,8-tetrakis(p-benzoate)pyrene (TBAPy).

13. The method of claim 12 wherein the single-site zirconium-benzyl derivative is tetrabenzylzirconium (ZrBn$_4$).

14. The method of claim 13 wherein the hafnium-based metal-organic framework has a formula Hf$_6$(OH)$_{16}$(TBAPy)$_2$.

15. The method of claim 14 wherein the compound has on average 2.4 Zr per Hf$_6$.

16. The method of to claim 14 wherein the compound has three Zr—O bonds and one Zr—Bn bonds.

17. The method of claim 9 wherein the compound is crystalline.

18. The method of claim 17 wherein the compound remains crystalline after the alkene is polymerized.

* * * * *